(12) United States Patent
Silva et al.

(10) Patent No.: US 7,754,919 B2
(45) Date of Patent: Jul. 13, 2010

(54) NON-NUCLEOSIDE REVERSE TRANSCRIPTASE INHIBITORS

(75) Inventors: Tania Silva, Sunnyvale, CA (US); Zachary Kevin Sweeney, Redwood City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 800 days.

(21) Appl. No.: 11/583,345

(22) Filed: Oct. 18, 2006

(65) Prior Publication Data

US 2007/0088015 A1    Apr. 19, 2007

Related U.S. Application Data

(60) Provisional application No. 60/728,609, filed on Oct. 19, 2005.

(51) Int. Cl.
*C07C 233/05* (2006.01)
*C07C 233/65* (2006.01)
*A61K 31/16* (2006.01)

(52) U.S. Cl. ............... 564/155; 514/522; 514/616; 558/415

(58) Field of Classification Search ......... 514/522, 514/616; 564/155; 558/415
See application file for complete search history.

(56) References Cited

U.S. PATENT DOCUMENTS

2005/0239881 A1   10/2005   Dunn et al.

OTHER PUBLICATIONS

Milton et al. Biaryl acids: Novel non-nucleoside inhibitors of HIV reverse transcriptase types 1 and 2, Bioorganic & Medicinal Chemistry Letters, 1998, vol. 8, pp. 2623,2628.*
Wyatt, PG., et al. Benzophenone Derivatives: A Novel Series of Potent and Selective Inhibitors of Human Immunodeficiency Virus Type 1 Reverse Transcriptase, *J. Med. Chem.* 1995, 38 (10) pp. 1657-1665.

* cited by examiner

*Primary Examiner*—Shailendra Kumar
(74) *Attorney, Agent, or Firm*—Brian L. Buckwalter

(57) ABSTRACT

The present invention provides for compounds useful for treating an HIV-1 infection, or preventing an HIV-1 infection, or treating AIDS or ARC. The compounds of the invention are of formula I wherein $R^1$, $R^2$, $R^3$, $R^4$, $R^5$ and X are as herein defined. Also disclosed in the present invention are methods of treating an HIV infection with compounds defined herein and pharmaceutical compositions containing said compounds.

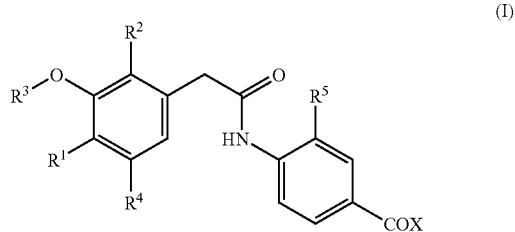

(I)

14 Claims, No Drawings

NON-NUCLEOSIDE REVERSE TRANSCRIPTASE INHIBITORS

CROSS REFERENCE TO PRIOR APPLICATIONS

This application claims the benefit of priority to U.S. Ser. No. 60/728,609 filed Oct. 19, 2005 the contents of which are hereby incorporated in their entirety by reference.

FIELD OF THE INVENTION

The invention relates to the field of antiviral therapy and, in particular, to non-nucleoside compounds that inhibit HIV-1 reverse transcriptase and are useful for treating Human Immunodeficiency Virus (HIV-1) mediated diseases. The invention provides novel N-phenyl phenylacetamide compounds according to formula I, for treatment or prophylaxis of HIV-1 mediated diseases, AIDS or ARC, employing said compounds in monotherapy or in combination therapy.

BACKGROUND OF THE INVENTION

The human immunodeficiency virus HIV-1 is the causative agent of acquired immunodeficiency syndrome (AIDS), a disease characterized by the destruction of the immune system, particularly of the $CD4^+$T-cell, with attendant susceptibility to opportunistic infections. HIV-1 infection is also associated with a precursor AIDS-related complex (ARC), a syndrome characterized by symptoms such as persistent generalized lymphadenopathy, fever and weight loss.

In common with other retroviruses, the HIV-1 genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV-1 reverse transcriptase. (J. S. G. Montaner et al. *Antiretroviral therapy: 'the state of the art'*, Biomed & Pharmacother. 1999 53:63-72; R. W. Shafer and D. A. Vuitton, *Highly active retroviral therapy* (HAART) *for the treatment of infection with human immunodeficiency virus type*, Biomed. & Pharmacother. 1999 53:73-86; E. De Clercq, *New Developments in Anti-HIV Chemotherap*. Curr. Med. Chem. 2001 8:1543-1572). Two general classes of reverse transcriptase inhibitors (RTI) have been identified: nucleoside reverse transcriptase inhibitors (NRTI) and non-nucleoside reverse transcriptase inhibitors (NNRTI). Currently the CCR5 co-receptor has emerged as a potential target for anti-HIV chemotherapy (D. Chantry *Expert Opin. Emerg. Drugs* 2004 9(1): 1-7; C. G. Barber *Curr. Opin. Invest. Drugs* 2004 5(8):851-861; D. Schols *Curr. Topics Med. Chem.* 2004 4(9):883-893; N. A. Meanwell and J. F. Kadow *Curr. Opin. Drug Discov. Dev.* 2003 6(4):451-461).

NRTIs typically are 2', 3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV-1 reverse transcriptase thereby altering the shape of the active site or blocking polymerase activity (R. W. Buckheit, Jr., *Non-nucleoside reverse transcriptase inhibitors: perspectives for novel therapeutic compounds and strategies for treatment of HIV infection*, Expert Opin. Investig. Drugs 200110(8)1423-1442; E. De Clercq *The role of non-nucleoside reverse transcriptase inhibitors (NNRTIs) in the therapy of HIV infection*, Antiviral Res. 1998 38:153-179; E. De Clercq *New Developments in Anti-HIV Chemotherapy*, Current medicinal Chem. 2001 8(13): 1543-1572; G. Moyle, *The Emerging Roles of Non-Nucleoside Reverse Transcriptase Inhibitors in Antiviral Therapy*, Drugs 2001 61 (1): 19-26). Although over thirty structural classes of NNRTIs have been identified in the laboratory, only three compounds have been approved for HIV-1 therapy: efavirenz, nevirapine and delavirdine.

Initially viewed as a promising class of compounds, in vitro and in vivo studies quickly revealed the NNRTIs presented a low barrier to the emergence of drug resistant HIV-1 strains and class-specific toxicity. Drug resistance frequently develops with only a single point mutation in the RT. While combination therapy with NRTIs, PIs and NNRTIs has, in many cases, dramatically lowered viral loads and slowed disease progression, significant therapeutic problems remain. (R. M. Gulick, *Eur. Soc. Clin. Microbiol. and Inf. Dis.* 2003 9(3): 186-193) The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV.

Certain N-phenyl phenylacetamide compounds have been found to have a variety of pharmacological properties.

US 20030187068 (H. Miyachi et al.) discloses N-phenyl phenylacetamide compounds which are peroxisome proliferators-activated receptor (PPARα) ligands.

US 20030220241 (D. Defoe-Jones et al.) disclose N-phenyl phenylacetamide compounds use to prepare protein conjugates with a prenyl protein transferase which are cleaved by prostate-specific antigen and are useful for treating cancer. W09917777 (J. S. Desolms et al.) teach prenyl protein transferase compounds which include N-phenyl phenylacetamides.

N-(substituted)phenyl 3-phenoxy-phenylacetamide compounds have been disclosed in WO01/21596 (A. A. Mortlock et al.)as inhibitors of aurora 2 kinase which are potentially useful in the treatment of proliferative diseases.

N-phenyl 3-(substituted)phenoxy-phenylacetamide compounds have be disclosed in WO2000059930 as inhibitors of prenyl protein transferase.

N-(substituted)phenyl3-phenoxy-phenylacetamide compounds have been disclosed in US2003011435 (K. Tani et al.) as EP4 receptor antagonists which are potentially useful in the suppression of TNF-α production and induction of IL-10 production.

Benzanilide compounds have been disclosed in W09965874 (Y. Ohtake et al.) as vasopressin antagonists.

N-phenyl phenylacetamide compounds 1 wherein $R^1$ can be substituted aryl, X can be O, n can be 0, $R^4$ and $R^5$ can be hydrogen have been disclosed in WO9315043 (T. Oe et al.) as acetyl CoA cholesterol O-acyltransferase inhibitors useful for reducing blood lipid levels and for treating arteriosclerosis.

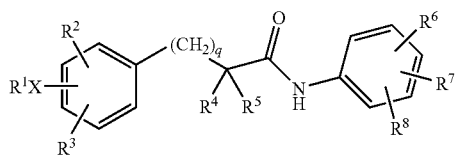

N-Phenyl phenylacetamides have also been used as synthetic intermediates for the preparation of pharmacologically active compounds. N-(2-carboalkoxy-5-chloro-phenyl) phenylacetamides (A. Kreimeyer et al., *J Med. Chem.* 1999 42:4394-4404; J. J. Kulagowski et al., *J. Med. Chem.* 1994 37:1402-1405 K. Ackermann et al., WO 97/26244), N-(2-cyano-5-chloro-phenyl) phenylacetamides (M. Rowley et al., *J. Med. Chem.* 1997 40:4053-4068; R. W. Carling et al., *J. Med. Chem.*, 1997 40:754-765 and N-(2-nitrophenyl) phenylacetamides (J. F. W. Keana et al., WO 96/22990) have been disclosed and utilized as intermediates for the synthesis of ligands for the glycine site on the N-methyl-D-aspartate (NMDA)receptor. NMDA ligands have been investigated for treating CNS disorders thought to be related neuronal death caused by over-stimulation of the post synaptic receptor sensitive to N-methyl-D-aspartic acid. Such disorders include Alzheimer's disease, epilepsy and cerebral ischemia. These compounds and indications are unrelated to the present invention.

2-Benzoyl phenyl-N-[phenyl]-acetamide compounds 2a and 2b have been shown to inhibit HIV-1 reverse transcriptase (P. G. Wyatt et al., *J. Med. Chem.* 1995 38(10):1657-1665). Further screening identified related compounds, e.g. 2-benzoyl phenyloxy-N-[phenyl]-acetamide, 3a, and a sulfonamide derivative 3b which also inhibited reverse transcriptase (J. H. Chan et al., *J. Med Chem.* 2004 47(5):1175-1182; C. L. Webster et al., WO01/17982).

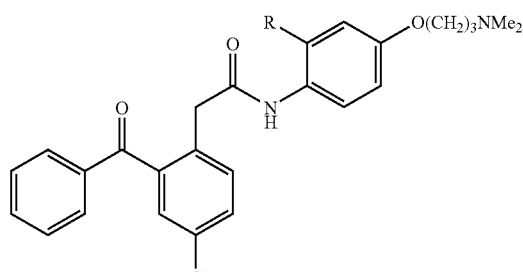

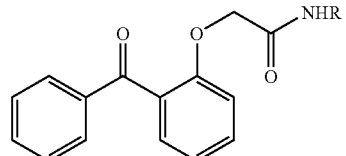

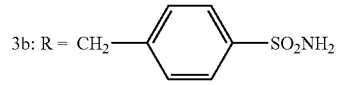

Pyridazinone non-nucleoside reverse transcriptase inhibitors 1 have been described by J. P. Dunn et al. in U. S. Publication 20040198736 filed Mar. 23, 2004 and by J. P. Dunn et al. in U. S. Publication No. 2005021554 filed Mar. 22, 2005. 5-Aralkyl-2,4-dihydro-[1,2,4]triazol-3-one, 5-aralkyl-3H-[1,3,4]oxadiazol-2-one and 5-aralkyl-3H-[1,3,4]thiadiazol-2-one non-nucleoside reverse transcriptase inhibitors 2 have been disclosed by J. P. Dunn et al. in U. S. Publication No. 20040192704 filed Mar. 23,2004 and by J. P. Dunn et al. in U.S. Publication No. 20060025462 filed Jun. 27, 2005. Related compounds are disclosed by Y. D. Saito et al. in U.S. Ser. No. 60/722,335. Phenylacetamide non-nucleoside reverse transcriptase inhibitors have been disclosed by J. P. Dunn et al. in U.S. Ser. No. 11/112,591 filed Apr. 22, 2005 and methods for treating retroviral infection with phenylacetamide compounds have been disclosed by J. P. Dunn et al. in U.S. Publication No. 20050239881 filed Apr. 22, 2005; T. Mirzadegan and T. Silva in U.S. Ser. No. 60/728,443 filed Oct. 19, 2005; and Z. K. Sweeney and T. Silva in U.S. Ser. No 60/728,609 filed ##. These applications are hereby incorporated by reference in their entirety.

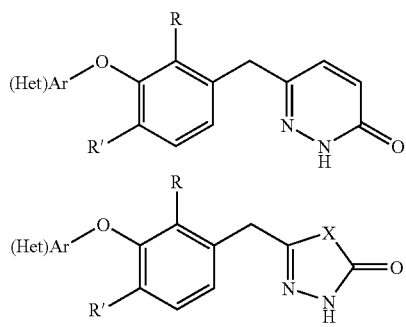

5: X = NH, O, S

In WO2006/067587 published Jun. 26, 2006, L. H. Jones et al. disclose biaryl ether derivatives of formula 6 and compositions containing them which bind to the enzyme reverse transcriptase and are modulators, especially inhibitors, thereof.

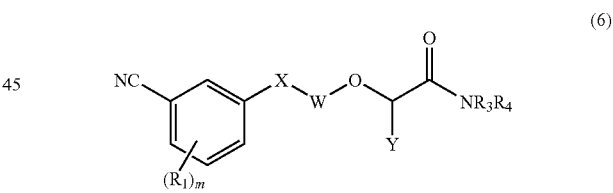

SUMMARY OF THE INVENTION

The present invention relates to compounds of formula I wherein:

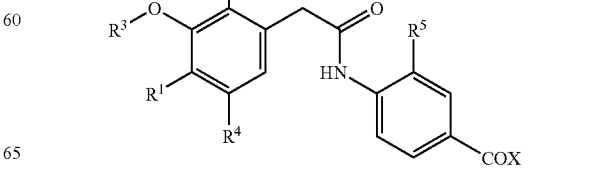

$R^1$ is halogen, $C_{1-6}$ alkyl, $C_{3-7}$ cycloalkyl, $C_{1-6}$ alkoxy, nitro or amino;

$R^2$ is hydrogen or fluorine $R^3$ is phenyl substituted with one to three substituents independently selected from the group consisting of $C_{1-6}$ alkyl, $C_{1-6}$ haloalkyl, $C_{3-8}$ cycloalkyl, halogen, cyano or nitro;

$R^4$ is hydrogen, $C_{1-6}$ alkyl or halogen;

$R^5$ is hydrogen, $C_{1-6}$ alkyl, $C_{3-7}$ cycloalkyl or halogen;

$R^6$ and $R^7$ are hydrogen, $C_{1-6}$ alkyl, $S(O)_2 C_{1-6}$ alkyl or $C_{1-3}$ acyl;

X is OH, $C_{1-6}$ alkoxy or $NR^a R^b$;

One of $R^a$ or $R^b$ is hydrogen, $C_{1-6}$ alkyl, $C_{3-6}$ cycloalkyl or $C_{1-6}$ hydroxyalkyl and the other of $R^a$ or $R^b$ is selected from the group consisting of (a) hydrogen,
(b) $C_{1-6}$ alkyl,
(c) $C_{1-6}$ hydroxyalkyl,
(d) $C_{1-6}$ carboxyalkyl,
(e) (alkylene)$_r NR^c R^d$,
(f) $S(O)_2$-$C_{1-6}$ alkyl,
(g) pyridinyl methyl,
(h) heterocyclylalkyl wherein said heterocyclyl is a group A1, A2, A3, A4 or A5:

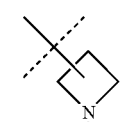

A1

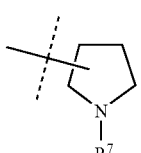

A2

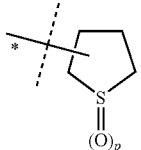

A3

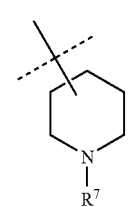

A4

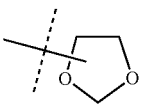

A5 said heterocyclyl group is optionally substituted with 1 to 3 groups selected from the group consisting of $C_{1-3}$ alkyl, halogen, or hydroxyl, (i) $C(=NR^e)NR^f R^g$ wherein (i)$R^e$, $R^f$ and $R^g$ are independently hydrogen or $C_{1-3}$ alkyl or (ii) either $R^e$ and $R^f$ or $R^f$ and $R^g$ together are $C_{2-3}$ alkylene and the remaining of $R^e$, $R^g$ and $R^f$ is hydrogen of $C_{1-3}$ alkyl, (j) a group B

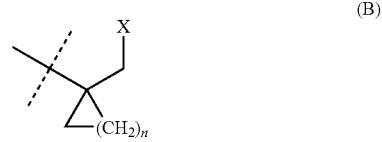

(B)

wherein n is an integer from 1 to 4 and X is as defined above, (k) $(CH_2)_n S(O)_2 (C_{1-3}$ alkyl) wherein n is an integer from 2 to 5, and, (k) $NR^c R^d$;

or $R^a$ and $R^b$ together with the nitrogen atom to which they are attached form a pyrrolidine, piperidine or azepine ring said pyrrolidine, piperidine or azepine ring optionally substituted with 1 to 3 groups independently selected from hydroxy, amino, $C_{1-3}$ alkylamine or $C_{1-3}$ dialkylamine, carboxyl, halogen and $C_{1-3}$ alkyl;

or, $R^a$ and $R^b$ together are $(CH_2)_m X^1 (CH_2)_n$ where m and n are both at least one and m+n is 3 to 5; or $R^a$ and $R^b$ together with the nitrogen atom to which they are attached form a pyrrolidine or a piperidine ring substituted with a carboxylic acid;

$R^c$ or $R^d$ are independently hydrogen or $C_{1-6}$ alkyl, or $R^c$ and $R^d$ together with the nitrogen atom to which they are attached form a pyrrolidine, piperidine or azepine ring said pyrrolidine, piperidine or azepine ring optionally substituted with 1 to 3 groups independently selected from hydroxy, amino, $C_{1-3}$ alkylamine or $C_{1-3}$ dialkylamine, carboxyl, halogen and $C_{1-3}$ alkyl; or $R^c$ and $R^d$ together are $(CH_2)_m X^1 (CH_2)_n$ where m and n are both at least one and m+n is 3 to 5.

$X^1$ is O, $S(O)_p$ or $NR^6$;

p is an integer from zero to two;

r is an integer from two to six; or, pharmaceutically acceptable salts thereof.

Compounds of formula I are useful inhibitors of HIV-1 reverse transcriptase and afford a method for prevention and treatment of HIV-1 infections and the treatment of AIDS and/or ARC. HIV undergoes facile mutations of its genetic code resulting in strains with reduced susceptibility to therapy with current therapeutic options. The present invention also relates to compositions containing compounds of formula I useful for the prevention and treatment of HIV-1 infections and the treatment of AIDS and/or ARC. The present invention further relates to compounds of formula I which are useful in mono therapy or combination therapy with other anti-viral agents.

DETAILED DESCRIPTION OF THE INVENTION

In one embodiment of the present invention there is provided a compound of formula I wherein $R^1$, $R^2$, $R^3$, $R^4$, $R^5$, $R^6$, $R^7$, $R^a$, $R^b$, $R^c$, $R^d$, $R^e$, $R^f$, X, $X^1$, A1, A2, A3, A4, A5, A5, B, m, n, p and r are as defined herein above. The phrase "as defined herein above" refers to the first definition for each group as provided in the Summary of the Invention. In other embodiments provided below, substituents present in each embodiment which are not explicitly defined retain the broadest definition provided in the Summary of the Invention.

In another embodiment of the present invention there is provided a compound according to formula I wherein X is $NR^aR^b$, $R^5$ is $C_{1-6}$ alkyl or halogen. In this embodiment either (i) $R^a$ is hydrogen and $R^b$ is hydrogen, $C_{1-6}$ alkyl, $C_{1-6}$ hydroxyalkyl, $(CH_2)_rNR^cR^d$, or pyridinyl methyl or (ii) $R^a$ and $R^b$ together with the nitrogen atom to which they are attached form a pyrrolidine, piperidine or azepine ring said pyrrolidine, piperidine or azepine ring optionally substituted with 1 to 3 groups independently selected from the group consisting of hydroxy, amino, $C_{1-3}$ alkylamine, $C_{1-3}$ dialkylamine, carboxyl, halogen and $C_{1-3}$ alkyl; or, (iii) $R^a$ and $R^b$ together are $(CH_2)_mX^1(CH_2)_n$ where m and n are both at least one and $3<m+n<5$; and r is 2 to 4.

In another embodiment of the present invention there is provided a compound according to formula I wherein X is $NR^aR^b$, $R^5$ is $C_{1-6}$ alkyl or halogen. In this embodiment either (i) $R^a$ is hydrogen and $R^b$ is hydrogen, $C_{1-6}$ alkyl, $C_{1-6}$ hydroxyalkyl, (alkylene)$_r$$NR^cR^d$, or pyridinyl methyl or (ii) $R^a$ and $R^b$ together with the nitrogen atom to which they are attached form a pyrrolidine, piperidine or azepine ring said pyrrolidine, piperidine or azepine ring optionally substituted with 1 to 3 groups independently selected from the group consisting of hydroxy, amino, $C_{1-3}$ alkylamine, $C_{1-3}$ dialkylamine, carboxyl, halogen and $C_{1-3}$ alkyl; or, (iii) $R^a$ and $R^b$ together are $(CH_2)_mX^1(CH_2)_n$ where m and n are two; and p is 2 and r is 2 to 4.

In another embodiment of the present invention there is provided a compound according to formula I wherein X is $NR^aR^b$ and $R^5$ is $C_{1-6}$ alkyl or halogen. In this embodiment either (i) $R^a$ is hydrogen and $R^b$ is $C_{1-6}$ carboxyalkyl or (ii) $R^a$ and $R^b$ together with the nitrogen atom to which they are attached form an optionally substituted pyrrolidine or piperidine ring.

In another embodiment of the present invention there is provided a compound according to formula I wherein X is $NR^aR^b$ and $R^5$ is $C_{1-6}$ alkyl or halogen. In this embodiment $R^a$ and $R^b$ together with the nitrogen atom to which they are attached form an optionally substituted pyrrolidine or piperidine ring.

In another embodiment of the present invention there is provided a compound according to formula I wherein X is $NR^aR^b$; $R^5$ is $C_{1-6}$ alkyl or halogen; $R^a$ is hydrogen or $C_{1-6}$ hydroxyalkyl; and, $R^b$ is $C_{1-6}$ hydroxyalkyl.

In another embodiment of the present invention there is provided a compound according to formula I wherein X is $NR^aR^b$; $R^5$ is $C_{1-6}$ alkyl or halogen; $R^a$ is hydrogen; and, $R^b$ is (alkylene)$_r$$NR^cR^d$.

In another embodiment of the present invention there is provided a compound according to formula I wherein X is $NR^aR^b$; $R^5$ is $C_{1-6}$ alkyl or halogen; $R^a$ is hydrogen; $R^b$ is (alkylene)$_r$$NR^cR^d$; and, r is 2 to 4.

In another embodiment of the present invention there is provided a compound according to formula I wherein X is $NR^aR^b$; $R^5$ is $C_{1-6}$ alkyl or halogen; $R^a$ is hydrogen; and, $R^b$ is $S(O)_2C_{1-6}$ alkyl.

In another embodiment of the present invention there is provided a compound according to formula I wherein X is $NR^aR^b$; $R^5$ is $C_{1-6}$ alkyl or halogen. In this embodiment either (i) $R^a$ and $R^b$ together with the nitrogen atom to which they are attached form a pyrrolidine, piperidine or azepine ring said pyrrolidine, piperidine or azepine ring optionally substituted with 1 to 3 groups independently selected from the group consisting of hydroxy, amino, $C_{1-3}$ alkylamine, $C_{1-3}$ dialkylamine, carboxyl, halogen and $C_{1-3}$ alkyl; or, (ii) $R^a$ and $R^b$ together are $(CH_2)_mX^1(CH_2)_n$ where m and n are both at least one and $3<m+n<5$.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; and, $R^5$ is $C_{1-6}$ alkyl or halogen.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$; and,r is 2 to 6. In this embodiment either (i) $R^a$ is hydrogen or $C_{1-6}$ hydroxyalkyl, and $R^b$ is selected from the group consisting of hydrogen, $C_{1-6}$ alkyl, $C_{1-6}$ hydroxyalkyl, (alkylene)$_r$N $R^cR^d$ and pyridinyl methyl or (ii) $R^a$ and $R^b$ together with the nitrogen atom to which they are attached form a pyrrolidine, piperidine or azepine ring said pyrrolidine, piperidine or azepine ring optionally with 1 to 3 groups independently selected from the group consisting of hydroxy, amino, $C_{1-3}$ alkylamine, $C_{1-3}$ dialkylamine, carboxyl, halogen and $C_{1-3}$ alkyl; or, (iii) $R^a$ and $R^b$ together are $(CH_2)_mX^1(CH_2)_n$ where m and n are both at least one and m+n is 3 to 5.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$; and, r is 2 to 4. In this embodiment either (i) $R^a$ is hydrogen or $C_{1-6}$ hydroxyalkyl and $R^b$ is selected from the group consisting of hydrogen, $C_{1-6}$ alkyl, $C_{1-6}$ hydroxyalkyl, (alkylene)$_r$$NR^cR^d$ and pyridinyl methyl or (ii) $R^a$ and $R^b$ together with the nitrogen atom to which they are attached form a pyrrolidine, piperidine or azepine ring said pyrrolidine, piperidine or azepine ring optionally substituted with 1 to 3 groups independently selected from the group consisting of hydroxy, amino, $C_{1-3}$ alkylamine, $C_{1-3}$ dialkylamine, carboxyl, halogen and $C_{1-3}$ alkyl; or, (iii) $R^a$ and $R^b$ together are $(CH_2)_mX^1(CH_2)_n$ where m, n and r are two.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$; and, either (i) $R^a$ is hydrogen and $R^b$ is $C_{1-6}$ carboxyalkyl; or, (ii) $R^a$ and $R^b$ and the nitrogen atom to which they are attached form a pyrrolidine or a piperidine substituted with a carboxylic acid.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or nitro; $R^4$ is hydrogen; $R^5$ is $C_{1-6}$ alkyl or halogen; X is $NR^aR^b$. In this embodiment or $R^a$ and $R^b$ and the nitrogen atom to which they are attached form a pyrrolidine or a piperidine substituted with a carboxylic acid.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$; $R^a$ is hydrogen or $C_{1-6}$ hydroxyalkyl; and, $R^b$ is $C_{1-6}$ hydroxyalkyl.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$; $R^a$ is hydrogen; and, $R^b$ is (alkylene)$_n$$NR^cR^d$.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$; $R^a$ is hydrogen; and, $R^b$ is $S(O)_2$—$C_{1-6}$ alkyl.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$. In this embodiment either (i) $R^a$ and $R^b$ together with the nitrogen atom to which they are attached form a pyrrolidine, piperidine or azepine ring said pyrrolidine, piperidine or azepine ring optionally substituted with 1 to 3 groups independently selected from the group consisting of hydroxy, amino, $C_{1-3}$ alkylamine, $C_{1-3}$ dialkylamine, carboxyl, halogen and $C_{1-3}$ alkyl; or, (ii) $R^a$ and $R^b$ together are $(CH_2)_m X^1 (CH_2)_n$ where m and n are both at least one and $3<m+n<5$.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$. In this embodiment either (i) $R^a$ and $R^b$ together with the nitrogen atom to which they are attached form a pyrrolidine, piperidine or azepine ring said pyrrolidine, piperidine or azepine ring optionally substituted with 1 to 3 groups independently selected from the group consisting of hydroxy, amino, $C_{1-3}$ alkylamine, $C_{1-3}$ dialkylamine, carboxyl, halogen and $C_{1-3}$ alkyl; or, (ii) $R^{a\text{ and }Rb}$ together are $(CH_2)_m X^1 (CH_2)_n$ where m and n are two.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; X is $NR^aR^b$. In this embodiment either (i) $R^a$ and $R^b$ together with the nitrogen atom to which they are attached form a pyrrolidine ring optionally substituted with 1 to 3 groups independently selected from the group consisting of hydroxy, amino, $C_{1-3}$ alkylamine, $C_{1-3}$ dialkylamine, carboxyl, halogen and $C_{1-3}$ alkyl.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; $R^a$ is hydrogen and $R^b$ is a heterocyclyl alkyl wherein said heterocyclyl is a group A1, A2, A3 or A4 and said heterocyclyl group is optionally substituted with 1 to 3 groups selected from the group consisting of $C_{1-3}$ alkyl, halogen, or hydroxyl and n is an integer from 0 to 4.

In another embodiment of the present invention there is provided a compound according to formula I wherein $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; $R^5$ is $C_{1-6}$ alkyl or halogen; $R^a$ is hydrogen and $R^b$ is $C(=NR^e)NR^fR^g$ wherein (i) $R^e$, $R^f$ and $R^g$ are independently hydrogen or $C_{1-3}$ alkyl or (ii) either $R^e$ and $R^f$ or $R^e$ and $R^g$ together are $C_{2-3}$ alkylene and the remaining of $R^e$, $R^g$ and $R^f$ is hydrogen of $C_{1-3}$ alkyl.

In another embodiment of the present invention there is provided a compound which is compound is selected from among compounds I-1 to I-58 in TABLE I In another embodiment of the present invention there is provided a method for treating an HIV-1 infection, or preventing an HIV-1 infection, or treating AIDS or ARC, comprising: administering to a host in need thereof a therapeutically effective amount of a compound according to formula I wherein (i) $R^1$, $R^2$, $R^3$, $R^4$, $R^5$, $R^6$, $R^7$, $R^a$, $R^b$, $R^c$, $R^d$, $R^d$, $R^e$, $R^f$, X, $X^1$, A1, A2, A3, A4, A5, A5, B, m, n, p and r are as defined herein above; or, (ii) $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; and, $R^5$ is $C_{1-6}$ alkyl or halogen; and, $R^6$, $R^7$, $R^a$, $R^b$, $R^c$, $R^d$, $R^e$, $R^f$, $R^g$, X, $X^1$, A1, A2, A3, A4, A5, B, m, n, p and r are as defined herein above.

In another embodiment of the present invention there is provided a method for treating an HIV-1 infection, or preventing an HIV-1 infection, or treating AIDS or ARC, comprising: co-administering to a host in need thereof a therapeutically effective amount of a compound according to formula I wherein (i) $R^1$, $R^2$, $R^3$, $R^4$, $R^5$, $R^6$, $R^7$, $R^a$, $R^b$, $R^c$, $R^d$, $R^e$, $R^f$, X, $X^1$, A1, A2, A3, A4, A5, B, m, n, p and r are as defined herein above; or, (ii) $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; and, $R^5$ is $C_{1-6}$ alkyl or halogen; and, $R^6$, $R^7$, $R^a$, $R^b$, $R^c$, $R^d$, $R^e$, $R^f$, $R^g$, X, $X^1$, A1, A2, A3, A4, A5, B, m, n, p and r are as defined herein above; and at least one compound selected from the group consisting of HIV protease inhibitors, nucleoside reverse transcriptase inhibitors, non-nucleoside reverse transcriptase inhibitors, CCR5 antagonists and viral fusion inhibitors.

In another embodiment of the present invention there is provided a method for treating an HIV-1 infection, or preventing an HIV-1 infection, or treating AIDS or ARC, comprising: co-administering to a host in need thereof a therapeutically effective amount of a compound according to formula I wherein (i) $R^1$, $R^2$, $R^3$, $R^4$, $R^5$, $R^6$, $R^7$, $R^a$, $R^b$, $R^c$, $R^d$, $R^e$, $R^f$, $R^g$, X, $X^1$, A1, A2, A3, A4, A5, B, m, n, p and r are as defined herein above; or, (ii) $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; and, $R^5$ is $C_{1-6}$ alkyl or halogen; and, $R^6$, $R^7$, $R^a$, $R^b$, $R^c$, $R^d$, $R^e$, $R^f$, $R^g$, X, $X^1$, A1, A2, A3, A4, A5, B, m, n, p and r are as defined herein above; and at least one compound selected from the group consisting of zidovudine, lamivudine, didanosine, zalcitabine, stavudine, rescriptor, sustiva, viramune, efavirenz, nevirapine, delavirdine, saquinavir, ritonavir, nelfinavir, indinavir, amprenavir, lopinavir and enfuvirtide (FUZEON®).

In another embodiment of the present invention there is provided a method for inhibiting HIV-1 reverse transcriptase comprising administering a compound according to formula I wherein (i) $R^1$, $R^2$, $R^3$, $R^4$, $R^5$, $R^6$, $R^7$, $R^a$, $R^b$, $R^c$, $R^d$, $R^e$, $R^f$, X, $X^1$, A1, A2, A3, A4, A5, B, m, n, p, and r are as defined herein above; or, (ii) $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; and, $R^5$ is $C_{1-6}$ alkyl or halogen; and, $R^6$, $R^7$, $R^a$, $R^b$, $R^c$, $R^d$, $R^e$, $R^f$, $R^g$, X, $X^1$, A1, A2, A3, A4, A5, B, m, n, p and r are as defined herein above.

In another embodiment of the present invention there is provided a method for inhibiting HIV-1 reverse transcriptase with at least one mutation compared to wild type RT comprising administering a compound according to formula I wherein (i) $R^1$, $R^2$, $R^3$, $R^4$, $R^5$, $R^6$, $R^7$, $R^a$, $R^b$, $R^c$, $R^d$, $R^e$, $R^f$, X, $X^1$, A1, A2, A3, A4, A5, B, m, n, p and r are as defined herein above; or, (ii) $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; and, $R^5$ is $C_{1-6}$ alkyl or halogen; and, $R^6$, $R^7$, $R^{a, Rb, Rc}$, $R^d$, $R^e$, $R^f$, $R^g$, X, $X^1$, A1, A2, A3, A4, A5, B, m, n, p and r are as defined herein above.

In another embodiment of the present invention there is provided a method for inhibiting HIV-1 reverse transcriptase which exhibits reduced susceptibility to efavirenz, nevirapine or delavirdine compared to wild type RT comprising administering a compound according to formula I wherein (i) $R^1$, $R^2$, $R^3$, $R^4$, $R^5$, $R^6$, $R^7$, $R^a$, $R^b$, $R^c$, $R^d$, $R^e$, $R^f$, X, $X^1$, A1, A2, A3, A4, A5, B, m, n, p, and r are as defined herein above; or, (ii) $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; and, $R^5$ is $C_{1-6}$ alkyl or halogen; and, $R^6$, $R^7$, $R^a$, $R^b$, $R^c$, $R^d$, $R^e$, $R^f$, $R^g$, X, $X^1$, A1, A2, A3, A4, A5, B, m, n, p and r are as defined herein above.

In another embodiment of the present invention there is provide a pharmaceutical composition for treating an HIV-1 infection, or preventing an HIV-1 infection, or treating AIDS or ARC, comprising a therapeutically effective quantity of a compound according to formula I wherein (i) $R^1$, $R^2$, $R^3$, $R^4$, $R^5$, $R^6$, $R^7$, $R^a$, $R^b$, $R^c$, $R^d$, $R^e$, $R^f$, X, $X^1$, A1, A2, A3, A4, A5, B, m, n, p, and r are as defined herein above; or, (ii) $R^1$ is halogen or $C_{1-6}$ alkyl; $R^2$ is fluorine; $R^3$ is phenyl substituted with one to three substituents independently selected from the group consisting of halogen, cyano or $C_{1-3}$ haloalkyl; $R^4$ is hydrogen; and, $R^5$ is $C_{1-6}$ alkyl or halogen; and, $R^6$, $R^7$, $R^a$, $R^b$, $R^c$, $R^d$, $R^e$, $R^f$, X, $X^1$, A1, A2, A3, A4, A5, B, m, n, p, and r are as defined herein above; admixed with at least one carrier, excipient or diluent.

In another embodiment of the present invention there is provided a compound according to formula I wherein (i) one of $R^a$ or $R^b$ is hydrogen or $C_{1-6}$ alkyl and the other of $R^a$ or $R^b$ is selected from the group consisting of (a) hydrogen, (b) $C_{1-6}$ alkyl, (c) $C_{1-6}$ hydroxyalkyl, (d) $C_{1-6}$ carboxyalkyl, (e) $(CH_2)_rNR^cR^d$, (f) $S(O)_2-C_{1-6}$ alkyl, and (g) pyridinyl methyl and (h) $(CH_2)_rS(O)_2(C_3$ alkyl), or (ii)$R^a$ and $R^b$ together with the nitrogen atom to which they are attached form a pyrrolidine, piperidine or azepine ring said pyrrolidine, piperidine or azepine ring optionally substituted with hydroxy, amino, $C_{1-3}$ alkylamine or $C_{1-3}$ dialkylamine or carboxyl; (iii) or, $R^a$ and $R^b$ together are $(CH_2)_mX^1(CH_2)_n$ where m and n are both at least one and m+n is 3 to 5; or $R^a$ and $R^b$ together with the nitrogen atom to which they are attached form a pyrrolidine or a piperidine ring substituted with a carboxylic acid; (i) one of $R^c$ or $R^d$ is hydrogen or $C_{1-6}$ alkyl and the other of $R^c$ or $R^d$ is selected from the group consisting of hydrogen and $C_{1-6}$ alkyl, or (ii) $R^c$ and $R^d$ together with the nitrogen atom to which they are attached form a pyrrolidine, piperidine or azepine ring said pyrrolidine, piperidine or azepine ring optionally substituted with hydroxy, amino, $C_{1-3}$ alkylamine or $C_{1-3}$ dialkylamine or carboxyl, or (iii) $R^c$ and $R^d$ together are $(CH_2)_mX^1(CH_2)_n$ where m and n are both at least one and m+n is 3 to 5 and $R^1$, $R^2$, $R^3$, $R^4$, $R^5$, $R^6$, X, $X^1$, m, n, p and r are as defined herein above. The embodiments described previously can also incorporate these definitions of $R^a$, $R^b$, $R^c$ and $R^d$ in this embodiment in place of the definitions in the summary of the invention.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. The term "heterocyclylalkyl" refers to an alkyl group having one to two heterocyclic substituents. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl refers to either an aryl or a heteroaryl group.

"Optional" or "optionally" means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "acyl" as used herein denotes a group of formula —C(=O)R wherein R is hydrogen or lower alkyl as defined herein. $C_{1-3}$ acyl denotes an acyl group as defied herein wherein R is $C_{1-3}$ alkyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons.

The terms "amino", "alkylamino" and "dialkylamino" as used herein refer to —$NH_2$, —NHR and —$NR_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to $NH_2$(alkylene)-, RHN(alkylene)-, and $R_2N$(alkylene)-respectively wherein R is alkyl, and both alkylene and alkyl are as defined herein. "$C_{1-10}$ alkylamino" as used herein refers to an aminoalkyl wherein alkyl is $C_{1-10}$. "$C_{1-10}$ alkyl-amino-$C_{2-6}$ alkyl" as used herein refers to a $C_{1-10}$ alkylamino(alkylene)$_{2-6}$ wherein alkyl is $C_{1-10}$ and the alkylene is $(CH_2)_{2-6}$. When the alkylene group contains three or more carbon atoms, the alkylene can be linear, e.g. —$(CH_2)_4$— or branched, e.g., —$(CMe_2CH_2)$—. The term "phenylamino" as used herein refers to -NHPh wherein Ph represents an optionally substituted phenyl group.

The term "alkylene" as used herein denotes a divalent saturated linear hydrocarbon radical of 1 to 10 carbon atoms (e.g., $(CH_2)_6$) or a branched saturated divalent hydrocarbon radical of 2 to 10 carbon atoms (e.g., —CHMe- or —$CH_2CH$(i-Pr)$CH_2$—), unless otherwise indicated. The open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" refers to an —O-alkyl wherein alkyl is $C_{1-10}$.

The term "cyano" as used herein refers to a carbon linked to a nitrogen by a triple bond, i.e., —C≡N. The term "nitro" as used herein refers to a group -$NO_2$.

The term "haloalkyl" as used herein denotes an unbranched or branched chain alkyl group as defined above wherein 1, 2, 3 or more hydrogen atoms are substituted by a halogen. "$C_{1-3}$ haloalkyl" as used herein refers to a haloalkyl composed of 1 to 3 carbons and 1-8 halogen substituents. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. $C_{1-6}$ hydroxyalkyl refers to a $C_{1-6}$ alkyl group as herein defined wherein one to three hydrogen atoms on different carbon atoms is/are replaced by a hydroxyl groups.

The term "$C_{1-6}$ carboxyalkyl" as used herein refers to a $C_{1-6}$ alkyl group as herein defined wherein one or two hydrogen atoms on different carbon atoms is/are replaced by a hydroxyl groups. The group $NR^aR^b$ as used in claim 1 where $R^a$ is a carboxyalkyl group which includes, but is not limited to, the natural amino acids glycine, alanine, valine, leucine and isoleucine.

The term "heterocycloalkyl" ( or "heterocyclylalkyl" ) denotes the radical of the formula R'R", wherein R' is a heterocyclic radical as defined herein, and R" is an alkylene radical as defined herein and the attachment point of the heterocycloalkyl radical will be on the alkylene radical. Examples of heterocycloalkyl radicals include, but are not limited to, 1-piperazinylmethyl, 2-morpholinomethyl, and the like. Heterocyclyl $C_{1-6}$ alkyl denotes a heterocyclylalkyl moiety wherein the alkylene chain is 1 to 6 carbons.

The terms "pyrrolidine", "piperidine" and "azepine" refer to a 5-, 6- or 7-membered cycloalkane respectively wherein one carbon atom is replaced by a nitrogen atom.

The term "amino acid" as used herein refers to naturally occurring and synthetic α, β, γ or δ amino acids, and includes but naturally occurring amino acids, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. Unless otherwise specified the amino acid can be in the L- or D-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β.-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β.-asparaginyl, β-glutaminyl, βaspartoyl, β-glutaroyl, β-lysinyl, β-argininyl or β-histidinyl. When the term amino acid is used, it is considered to be a specific and independent disclosure of each of the esters of α, β, γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The phrase "side chain of a naturally occurring amino acid" denotes hydrogen, methyl, iso-propyl, iso-butyl, sec-butyl, —$CH_2OH$, —$CH(OH)CH_3$, —$CH_2SH$, —$CH_2CH_2SMe$, —$(CH_2)pCOR$ wherein R is —OH or —$NH_2$ and p is 1 or 2, —$(CH_2)_q$—$NH_2$ where q is 3 or 4, —$(CH_2)_3$—NHC(=NH)$NH_2$, —$CH_2C_6H_5$, —$CH_2$-p-$C_6H_4$—OH, (3-indolinyl)methylene, (4-imidazolyl)methylene.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

The term "wild type" as used herein refers to the HIV-1 virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system The term "nucleoside and nucleotide reverse transcriptase inhibitors" ("NRTI's) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT; RETROVIR®) from GSK; didanosine (ddI; VIDEX®) from Bristol-Myers Squibb Co. (BMS); zalcitabine (ddC; HIVID®) from Roche; stavudine (d4T; ZERIT®) from BMS; lamivudine (3TC; EPWVIR®) from GSK; abacavir (1592U89; ZIAGEN®) disclosed in WO96/30025 and available from GSK; adefovir dipivoxil (bis(POM)-PMEA; PREVON®) Gilead Sciences; lobucavir (BMS-180194), a nucleoside reverse transcriptase inhibitor disclosed in EP-0358154 and EP-0736533 and under development by BMS; BCH-10652, a reverse transcriptase inhibitor (in the form of a racemic mixture of BCH-10618 and BCH-10619) under development by Biochem Pharma; emitricitabine [(−)-FTC] licensed from Emory University under Emory Univ. U.S. Pat. No. 5,814, 639 and under development by Gilead Sciences, Inc; Evucitabine (β-L-D4FC; β-L-2', 3'-dideoxy-5-fluoro-cytidene)

licensed by Yale University to Vion Pharmaceuticals; DAPD, the purine nucleoside, (−)-β-D-2,6,-diamino-purine dioxolane disclosed in EP-0656778 and licensed by Emory University and the University of Georgia to Triangle Pharmaceuticals; and Iodenosine (FddA), 9-(2,3-dideoxy-2-fluoro-β-D-threo-pentofuranosyl)adenine, an acid stable purine-based reverse transcriptase inhibitor discovered by the NIH and under development by U.S. Bioscience Inc.

Three NNRTIs have been approved in the USA: nevirapine (BI-RG-587; VIRAMUNE®) available from Boehringer Ingelheim (BI); delaviradine (BHAP, U-90152; RESCRIPTOR®) available from Pfizer; efavirenz (DMP-266, SUSTIVA®) a benzoxazin-2-one from BMS. Other NNRTIs currently under investigation include PNU-142721, a furopyridine-thio-pyrimide under development by Pfizer; capravirine (S-1153 or AG-1549; 5-(3,5-dichlorophenyl)-thio-4-isopropyl-1-(4-pyridyl)methyl-1H-imidazol-2- ylmethyl carbonate) by Shionogi and Pfizer; emivirine [MKC-442; (1-(ethoxy-methyl)-5-(1-methylethyl)-6-(phenylmethyl)-(2,4(1H,3H)-pyrimidinedione)] by Mitsubishi Chemical Co. and Triangle Pharmaceuticals; (+)-calanolide A (NSC-675451) and B, coumarin derivatives disclosed in NIH U.S. Pat. No. 5,489,697, licensed to Sarawak/Advanced Life Sciences; etravirine (TMC-125; 4-[6-amino-5-bromo-2-(4-cyano-phenylamino)-pyrimidin-4-yloxy]-3,5-dimethyl-benzonitrile) and DAPY (TMC120; 4- {4-[4-((E)-2-cyano-vinyl)-2,6-dimethyl-phenylamino]-pyrimidin-2-ylamino}-benzonitrile) by Tibotec-Virco and Johnson & Johnson; BILR-355 BS (12-ethyl-8-[2-(1-hydroxy-quinolin-4-yloxy)-ethyl]-5-methyl-11,12-dihydro-5H-1,5,10,12-tetraaza-dibenzo[a,e]cycloocten-6-one by Boehringer-Ingleheim; PHI-236 (7-bromo-3-[2-(2,5-dimethoxy-phenyl) -ethyl]-3,4-dihydro-1H-pyrido[1,2 -a][1,3,5]triazine-2-thione) and PHI-443 (TMC-278, 1-(5-bromo-pyridin-2-yl)-3-(2-thiophen-2-yl-ethyl)-thiourea) by Paradigm Pharmaceuticals.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN® as well as nonpeptide protease inhibitors e.g., VIRACEPT®.

Typical suitable PIs include saquinavir available in hard gel capsules as INVIRASE® and in soft gel capsules as FORTOVASE® from Roche; ritonavir (ABT-538) available as NORVIR-from Abbott Laboratories; Lopinavir (ABT-378) also available from Abbot; KALETRA®, is co-formulation lopinavir and a sub-therapeutic dose of ritonavir available from Abbott Laboratories; indinavir (MK-639) available as CRIXIVAN® from Merck & Co.; nelfnavir (AG-1343) available as VIRACEPT® from Agouron Pharmaceuticals, Inc.; amprenavir (141W94) available as AGENERASE® from Vertex Pharmaceuticals, Inc. and GSK; tipranavir (PNU-140690) available as APTIVUS® from BI; lasinavir (BMS-234475/CGP-61755) by BMS; BMS-2322623, an azapeptide under development by BMS as a 2nd-generation HIV-1 PI; GW-640385X (VX-385) under development in a collaboration between GSK and Vertex; AG-001859 in preclinical development by Agouron/Pfizer; SM-309515 under development by Sumitomo Pharmaceuticals.

Additional PIs in preclinical development include N-cycloalkylglycines by BMS, α-hydroxyarylbutanamides by Enanta Pharmaceuticals; α-hydroxy-γ-[[(carbocyclic- or heterocyclic-substituted)amino)carbonyl]alkanamide derivatives; γ-hydroxy-2-(fluoroalkylaminocarbonyl)-1-piperazinepentanamides by Merck; dihydropyrone derivatives and α- and β-amino acid hydroxyethylamino sulfonamides by Pfizer; and N-aminoacid substituted L-lysine derivatives by Procyon.

Entry of HIV into target cells requires CD-4 cell surface receptor and the CC R5 (M-tropic strains)and CXCR4 (T-tropic strains) chemokine co-receptors. Chemokine antagonize which block viral binding to the chemokines are useful inhibitors of viral infection. Takeda's identified TAK-779 as a potential CCR5 antagonist. (M. Shiraishi et al., *J. Med. Chem.* 2000 43(10):2049-2063; M. Babba et al. *Proc. Nat. Acad Sci. USA* 1999 96:5698-5703) and TAK-220 (C. Tremblay et al. *Antimicrob. Agents Chemother.* 2005 49(8): 3483-3485). W00039125 (D. R. Armour et al.) and WO0190106 (M. Perros et al.) disclose heterocyclic compounds that are potent and selective CCR5 antagonists. Miraviroc (UK-427,857; MVC) has advanced by Pfizer to phase III clinical trials and show activity against HIV-1 isolates and laboratory strains (P. Dorr et al., *Antimicrob. Agents Chemother.* 2005 49(11):4721-4732; A. Wood and D. Armour, *Prog Med. Chem.* 2005 43:239-271; C. Watson et al., *Mol. Pharm.* 2005 67(4):1268-1282; M. J. Macartney et al., 43$^{rd}$ *Intersci. Conf Antimicrob. Agents Chemother.* Sep. 14-17, 2003, Abstract H-875). Schering has advanced Sch-351125 (SCH-C) into Phase I/II clinical studies and reported the advance of a more potent follow-up compound, Vicroviroc (Sch-417690, SCH-D) into Phase I studies. (S. W. McCrombie et al., WO00066559; B. M. Baroudy et al. WO00066558; A. Palani et al., *J. Med. Chem.* 2001 44(21): 3339-3342; J. R. Tagat et al., *J. Med. Chem.* 2001 44(21): 3343-3346; J. A. Esté, *Cur. Opin. Invest. Drugs* 2002 3(3): 379-383; J. M. Struzki et al. *Proc. Nat. Acad Sci. USA* 2001 98:12718-12723). Merck has disclosed the preparation of(2S)-2-(3-chlorophenyl)-1-N-(methyl)-N-(phenylsulfonyl)amino]-4-[spiro(2,3-dihydrobenzothiophene-3,4'-piperidin-1'-yl)butane S-oxide (1) and related derivatives with good affinity for the CCR5 receptor and potent-HIV activity. (P. E. Finke et al., *Bioorg. Med. Chem. Lett.*, 2001 11:265-270; P. E. Finke et al., *Bioorg. Med. Chem. Lett.*, 2001 11:2469-2475; P. E. Finke et al., *Bioorg. Med. Chem. Lett.*, 2001 11:2475-2479; J. J. Hale et al., *Bioorg. Med. Chem. Lett.*, 2001 11:2741-22745; D. Kim et al., *Bioorg. Med. Chem. Lett.*, 2001 11:3099-3102) C. L. Lynch et al. *Org Lett.* 2003 5:2473-2475; R. S. Veazey et al. *J Exp. Med* 2003 198: 1551-1562. GSK-873140 (ONO-4128, E-913, AK-602) was identified in a program initiated at Kumamoto University (K. Maeda et al. *J Biol. Chem.* 2001 276:35194-35200; H. Nakata et al. *J Virol.* 2005 79(4):2087-2096) and has been advanced to clinical trials. In WO00/166525; WO00/187839; WO02/076948; WO02/076948; WO02/079156, WO2002070749, WO2003080574, WO2003042178, WO2004056773, WO2004018425 Astra Zeneca disclose 4-amino piperidine compounds which are CCR5 antagonists. In U.S. Publication No. 20050176703 published Aug. 11, 2005, S. D. Gabriel and D. M. Rotstein disclosed heterocyclic CCR5 antagonist capable of prevent HIV cell entry. In U.S. Publication No. 20060014767 published Jan. 19, 2006, E. K. Lee et al. disclosed heterocyclic CCR5 antagonist capable of prevent HIV cell entry.

Attachment Inhibitors effectively block interaction between viral envelope proteins and chemokine receptors or CD40 protein.$_{13}$ TNX-355 is a humanized IgG4 monoclonal antibody that binds to a conformational epitope on domain 2 of CD4. (L. C. Burkly et al., *J Immunol.* 1992 149:1779-87) TNX-355 can inhibit viral attachment of CCR5-, CXCR4- and dual/mixed tropic HIV-1 strains. (E. Godofsky et al., In Vitro Activity of the Humanized Anti-CD4 Monoclonal Antibody, TNX-355, against CCR5, CXCR4, and Dual-Tropic Isolates and Synergy with Enfuvirtide, 45*th Annual Interscience Conference on Antimicrobial Agents and Chemotherapy (ICAAC)*. Dec. 16-19, 2005, Washington D.C. Abstract # 3844; D. Norris et al. TNX-355 in Combination with Optimized Background Regime (OBR) Exhibits Greater Antiviral Activity than OBR Alone in HIV-Treatment Experienced Patients, 45*th Annual Interscience Conference on Antimicrobial Agents and Chemotherapy (ICAAC)*. Dec. 16-19, 2005, Washington D.C. Abstract # 4020.).

Macromolecular therapeutics including antibodies, soluble receptors and biologically active fragments thereof have become an increasingly important adjunct to conventional low molecular weight drugs. (O. H. Brekke and I. Sandlie *Nature Review Drug Discov.* 2003 2:52-62; A. M. Reichert *Nature Biotech.* 2001 19:819-821) Antibodies with high specificity and affinity can be targeted at extra-cellular proteins essential for viral cell fusion. CD4, CCR5 and CXCR4 have been targets for antibodies which inhibit viral fusion.

V. Roschke et al. (Characterization of a Panel of Novel Human Monoclonal Antibodies that Specifically Antagonize CCR5 and Block HIV-1 Entry, 44*th Annual Interscience Conference on Antimicrobial Agents and Chemotherapy (ICAAC)*. Oct. 29, 2004, Washington D.C. Abstract # 2871) have disclosed monoclonal antibodies which bind to the CCR5 receptor and inhibit HIV-1 entry into cells expressing the CCR5 receptor. L. Wu and C. R. MacKay disclose in U.S. Ser. No. 09/870,932 filed May 30, 2001 disclose monoclonal antibodies 5C7 and 2D7 which bind to the CCR5 receptor in a manner capable of inhibiting HIV-1 infection of a cell. W. C. Olsen et al. (*J. Virol.* 1999 73(5):4145-4155) disclose monoclonal antibodies capable of inhibiting (i) HIV-1 cell entry, (ii) HIV-1 envelope-mediated membrane fusion, (iii) gp120 binding to CCR5 and (iv) CC-chemokine activity. Synergism between the anti-CCR5 antibody Pro 140 and a low molecular weight CCR5 antagonists have been disclosed by Murga et al. (3rd IAS Conference on HIV Pathogenesis and Treatment, Abstract TuOa.02.06. Jul. 24-27, 2005, Rio de Janeiro, Brazil) Anti-CCR5 antibodies have been isolated which inhibit HIV-1 cell entry also have been disclosed by M. Brandt et al. in U.S. Ser. No. 11/394,439 filed Mar31, 2006.

FUZEON® (T-20, DP-178, pentafuside) is disclosed in U.S. Pat. No. 5,464,933. T-20 and an analog, T-1249, are analogs of HIV-1 gp41 fragment which are effectively inhibit a conformational change required for HIV fusion. T-20 has been approved and is available from Roche and Trimeris. FUZEON is administered as a continuous sc infusion or injection in combination therapy with other classes of anti HIV drugs.

Other antiviral agents which may be useful in HIV therapy include hydroxyurea, ribavirin, IL-2, IL-12, pentafuside. Hydroyurea (Droxia), aribonucleoside triphosphatereductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PRO-LEUKIN® (aldesleukin) from Chiron Corp. as a lyophilized powder for IV infusion or sc administration. IL-12 is disclosed in WO96/25171 and is available from Roche and Wyeth Pharmaceuticals. Ribavirin, 1-β-D-ribofuranosyl-1H-1,2,4-triazole-3-carboxamide, is described in U.S. Pat. No. 4,211,771 and is available from ICN Pharmaceuticals.

Abbreviations used in this application include: acetyl (Ac), acetic acid (HOAc), azo-bis-isobutyrylnitrile (AIBN), 1-N-hydroxybenzotriazole (HOBt), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeS(O)_2$— (mesyl or Ms), 1,4-diazabicyclo[2.2.2]octane (DABCO), mass spectrum (ms) diethylaminosulfur trifluoride (DAST), methyl 1-butyl ether (MTBE), dibenzylideneacetone (Dba), N-carboxyanhydride (NCA), 1,5-diazabicyclo[4.3.0]non-5-ene (DBN), N-bromosuccinimide (NBS), N-chlorosuccinimide (NCS), 1,8-diazabicyclo[5.4.0]undec-7-ene (DBU), N-methylmorpholine (NMM), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), di-iso-propylethylamine (DIPEA), pyridine (pyr), di-iso-butylaluminumhydride, DIBAL-H, room temperature, rt or RT, N,N-dimethyl acetamide (DMA), tert-butyldimethylsilyl or t-$BuMe_2Si$, (TBDMS), 4-N,N-dimethylaminopyridine (DMAP), triethylamine ($Et_3N$ or TEA), N,N-dimethylformamide (DMF), triflate or $CF_3S(O)_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS), 4-Me-$C_6H_4S(O)_2$- or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. Larock, *Comprehensive Organic Transformations*, $2^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be recognized by one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and including, but not limited to mass spectrometry, nuclear magnetic resonance spectroscopy and infrared spectroscopy.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. One skilled in the art will be able to identify optimal reaction conditions for each transformation without undue experimentation.

While the following schemes often depict specific compounds; the reaction conditions are exemplary and can readily be adapted to other reactants. Alternative conditions also are well known. The reaction sequences in the following examples are not meant to limit the scope of the invention as set forth in the claims.

Examples of representative compounds encompassed by the present invention and within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

Some structures in the following schemes are depicted with generalized substituents; however, one skilled in the art will immediately appreciate that the nature of the R groups can be varied to afford the various compounds contemplated in this invention. Moreover, the reaction conditions are exemplary and alternative conditions are well known. The reaction sequences in the following examples are not meant to limit the scope of the invention as set forth in the claims. In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I

| Cpd. No. | NAME | mw | ms | mp |
|---|---|---|---|---|
| I-1 | 3-Chloro-4-{2-[3-(3-cyano-5-difluoromethyl-phenoxy)-2-fluoro-4-methyl-phenyl]-acetylamino}-benzoic acid | 488.85 | 488 | — |
| I-2 | 4-{2-[4-Chloro-3-(3-chloro-5-cyano-phenoxy)-2-fluoro-phenyl]-acetylamino}-3-methyl-benzamide | 472.3 | 471 | 255.9-257.1 |
| I-3 | 4-{2-[4-Chloro-3-(3-chloro-5-cyano-phenoxy)-2-fluoro-phenyl]-acetylamino}-3-methyl-benzoic acid | 473.29 | 472 | 287.1-289.1 |
| I-4 | 4-{2-[4-Chloro-3-(3-chloro-5-cyano-phenoxy)-2-fluoro-phenyl]-acetylamino}-N-(2-dimethylamino-ethyl)-3-methyl-benzamide | 543.42 | 542 | 213.3-216.0 |
| I-5 | 4-{2-[4-Chloro-3-(3-chloro-5-cyano-phenoxy)-2-fluoro-phenyl]-acetylamino}-N-(2-dimethylamino-ethyl)-3-methyl-benzamide; compound with trifluoro-acetic acid | 543.42 | 542 | — |
| I-6 | 2-[4-Chloro-3-(3-chloro-5-cyano-phenoxy)-2-fluoro-phenyl]-N-[2-methyl-4-(4-methyl-piperazine-1-carbonyl)-phenyl]-acetamide; compound with trifluoro-acetic acid | 555.43 | 554 | — |
| I-7 | 2-[4-Chloro-3-(3-chloro-5-cyano-phenoxy)-2-fluoro-phenyl]-N-[4-((R)-3-hydroxy-pyrrolidine-1-carbonyl)-2-methyl-phenyl]-acetamide | 542.39 | 542(M + 1) | — |
| I-8 | 4-{2-[4-Chloro-3-(3-chloro-5-cyano-phenoxy)-2-fluoro-phenyl]-acetylamino}-N-(2-hydroxy-ethyl)-3-methyl-benzamide | 516.35 | 516(M + 1) | — |
| I-9 | 4-{2-[4-Chloro-3-(3-chloro-5-cyano-phenoxy)-2-fluoro-phenyl]-acetylamino}-3-methyl-N-(4-methyl-piperazin-1-yl)-benzamide; compound with trifluoro-acetic acid | 570.45 | 570(M + 1) | — |
| I-10 | 4-{2-[4-Chloro-3-(3-chloro-5-cyano-phenoxy)-2-fluoro-phenyl]-acetylamino}-N-((R)-2-hydroxy-propyl)-3-methyl-benzamide | 530.38 | 530(M + 1) 528(M − 1) | 249.0-249.4 |
| I-11 | 2-[4-Chloro-3-(3-chloro-5-cyano-phenoxy)-2-fluoro-phenyl]-N-[4-(4-hydroxy-piperidine-1-carbonyl)-2-methyl-phenyl]-acetamide | 556.42 | 556(M + 1) | — |
| I-12 | 2-[4-Chloro-3-(3-chloro-5-cyano-phenoxy)-2-fluoro-phenyl]-N-[2-methyl-4-(morpholine-4-carbonyl)-phenyl]-acetamide | 542.39 | 542(M + 1) | — |

TABLE I-continued

| Cpd. No. | NAME | mw | ms | mp |
|---|---|---|---|---|
| I-13 | 4-{2-[4-Chloro-3-(3-chloro-5-cyano-phenoxy)-2-fluoro-phenyl]-acetylamino}-3-methyl-N-pyridin-4-ylmethyl-benzamide; compound with trifluoro-acetic acid | 563.41 | 563(M + 1) | — |
| I-14 | 4-{2-[4-Chloro-3-(3-chloro-5-cyano-phenoxy)-2-fluoro-phenyl]-acetylamino}-3-methyl-N-(2-pyrrolidin-1-yl-ethyl)-benzamide; compound with trifluoro-acetic acid | 569.46 | 569(M + 1) | — |
| I-15 | 4-{2-[4-Chloro-3-(3-chloro-5-cyano-phenoxy)-2-fluoro-phenyl]-acetylamino}-3-methyl-N-pyridin-3-ylmethyl-benzamide; compound with trifluoro-acetic acid | 563.41 | 563(M + 1) | — |
| I-16 | 4-{2-[4-Chloro-3-(3-chloro-5-cyano-phenoxy)-2-fluoro-phenyl]-acetylamino}-N-((R)-2,2-dimethyl-[1,3]dioxolan-4-ylmethyl)-3-methyl-benzamide | 586.44 | 5451[1] | — |
| I-17 | 4-{2-[4-Bromo-3-(3-cyano-5-difluoromethyl-phenoxy)-2-fluoro-phenyl]-acetylamino}-3-methyl-benzoic acid | 533.3 | 532 | 267.9-268.1 |
| I-18 | 4-{2-[4-Bromo-3-(3-cyano-5-difluoromethyl-phenoxy)-2-fluoro-phenyl]-acetylamino}-N-(2-dimethylamino-ethyl)-3-methyl-benzamide | 603.44 | 602 | 205.6-206.6 |
| I-19 | 3-Chloro-4-{2-[4-chloro-3-(3-chloro-5-cyano-phenoxy)-2-fluoro-phenyl]-acetylamino}-benzoic acid | 493.7 | 492 | 242.0-243.0 |
| I-20 | 4-{2-[4-Chloro-3-(3-chloro-5-cyano-phenoxy)-2-fluoro-phenyl]-acetylamino}-N-(2,3-dihydroxy-propyl)-3-methyl-benzamide | 546.38 | 545 | — |
| I-21 | 3-Chloro-4-{2-[4-chloro-3-(3-chloro-5-cyano-phenoxy)-2-fluoro-phenyl]-acetylamino}-N-(2-dimethylamino-ethyl)-benzamide | 563.84 | 562 | 202.8-203.6 |
| I-22 | 4-{2-[4-Bromo-3-(3-chloro-5-cyano-phenoxy)-2-fluoro-phenyl]-acetylamino}-3-methyl-benzoic acid | 517.74 | 516 | 270.0-270.8 |
| I-23 | 4-{2-[4-Chloro-3-(3-chloro-5-cyano-phenoxy)-2-fluoro-phenyl]-acetylamino}-3-methyl-N-(2-methylamino-ethyl)-benzamide | 529.4 | 528 | — |
| I-24 | 4-{2-[4-Bromo-3-(3-chloro-5-cyano-phenoxy)-2-fluoro-phenyl]-acetylamino}-N-[2-(1,1-dioxo-1$\lambda^6$-thiomorpholin-4-yl)-ethyl]-3-methyl-benzamide | 677.98 | 676 | 168.1-170.1 |
| I-25 | 4-{2-[4-Bromo-3-(3-chloro-5-cyano-phenoxy)-2-fluoro-phenyl]-acetylamino}-N-[2-(4-hydroxy-piperidin-1-yl)-ethyl]-3-methyl-benzamide | 643.94 | 642 | 219.6-221.6 |
| I-26 | 4-{2-[4-Bromo-3-(3-chloro-5-cyano-phenoxy)-2-fluoro-phenyl]-acetylamino}-N-(2-dimethylamino-1-methyl-ethyl)-3-methyl-benzamide | 601.9 | 600 | 222.0-223.2 |
| I-27 | 4-{2-[4-Bromo-3-(3-chloro-5-cyano-phenoxy)-2-fluoro-phenyl]-acetylamino}-3-methyl-N-(2-pyrrolidin-1-yl-ethyl)-benzamide | 613.91 | 612 | 214.7-216.9 |
| I-28 | 4-{2-[4-Bromo-3-(3-chloro-5-cyano-phenoxy)-2-fluoro-phenyl]-acetylamino}-3-methyl-N-(2-morpholin-4-yl-ethyl)-benzamide | 629.91 | 628 | 219.8-222.0 |
| I-29 | N-(2-Amino-ethyl)-4-{2-[4-chloro-3-(3-chloro-5-cyano-phenoxy)-2-fluoro-phenyl]-acetylamino}-3-methyl-benzamide | 515.37 | 514 | 207.6-208.6 |
| I-30 | 4-{2-[4-Bromo-3-(3-chloro-5-cyano-phenoxy)-2-fluoro-phenyl]-acetylamino}-3-methyl-N-(2-piperazin-1-yl-ethyl)-benzamide | 628.93 | 627 | 126.5-127.0 |

TABLE I-continued

| Cpd. No. | NAME | mw | ms | mp |
|---|---|---|---|---|
| I-31 | 4-{2-[4-Bromo-3-(3-chloro-5-cyano-phenoxy)-2-fluoro-phenyl]-acetylamino}-3-methyl-N-pyrrolidin-3-yl-benzamide | 585.86 | 584 | 117.8-120.0 |
| I-32 | 4-{2-[4-Bromo-3-(3-chloro-5-cyano-phenoxy)-2-fluoro-phenyl]-acetylamino}-3-chloro-N-(2-pyrrolidin-1-yl-ethyl)-benzamide | 634.33 | 632 | 197.7-198.3 |
| I-33 | 4-{2-[4-Bromo-3-(3-cyano-5-difluoromethyl-phenoxy)-2-fluoro-phenyl]-acetylamino}-3-chloro-N-(2-pyrrolidin-1-yl-ethyl)-benzamide | 649.89 | 648 | 160.0-165.7 |
| I-34 | 4-{2-[4-Bromo-3-(3-cyano-5-difluoromethyl-phenoxy)-2-fluoro-phenyl]-acetylamino}-3-methyl-N-(2-pyrrolidin-1-yl-ethyl)-benzamide | 629.47 | 628 | 202.4-203.7 |
| I-35 | 4-{2-[4-Bromo-3-(3-cyano-5-difluoromethyl-phenoxy)-2-fluoro-phenyl]-acetylamino}-N-((R)-2-hydroxy-propyl)-3-methyl-benzamide | 590.39 | 589 | 225.5-228.8 |
| I-36 | 2-[4-Bromo-3-(3-chloro-5-cyano-phenoxy)-2-fluoro-phenyl]-N-(4-methanesulfonylaminocarbonyl-2-methyl-phenyl)-acetamide | | | 244.9-246.7 |
| I-37 | 2-[4-Bromo-3-(3-chloro-5-cyano-phenoxy)-2-fluoro-phenyl]-N-(2-chloro-4-guanidinocarbonyl-phenyl)-acetamide | 579.21 | 577 | 207.0-209.0 |
| I-38 | 2-[4-Bromo-3-(3-chloro-5-cyano-phenoxy)-2-fluoro-phenyl]-N-(2-chloro-4-guanidinocarbonyl-phenyl)-acetamide; trifluoroacetic acid salt | 579.21 | 578 | |
| I-39 | N-(2-Amino-2-methyl-propyl)-4-{2-[4-bromo-3-(3-chloro-5-cyano-phenoxy)-2-fluoro-phenyl]-acetylamino}-3-chloro-benzamide | 608.29 | 607 | |
| I-40 | 4-{2-[4-Bromo-3-(3-chloro-5-cyano-phenoxy)-2-fluoro-phenyl]-acetylamino}-3-chloro-N-[2-(4,4-difluoro-piperidin-1-yl)-ethyl]-benzamide; hydrochloride salt | 684.34 | | 140.2-143.3 |
| I-41 | N-{2-[Bis-(2-hydroxy-ethyl)-amino]-ethyl}-4-{2-[4-bromo-3-(3-chloro-5-cyano-phenoxy)-2-fluoro-phenyl]-acetylamino}-3-chloro-benzamide | 668.34 | | 100.1 |
| I-42 | 4-{2-[4-Bromo-3-(3-chloro-5-cyano-phenoxy)-2-fluoro-phenyl]-acetylamino}-3-chloro-N-(2-dimethylamino-1-methyl-ethyl)-benzamide | 622.32 | | 190.1 |
| I-43 | 4-{2-[4-Bromo-3-(3-chloro-5-cyano-phenoxy)-2-fluoro-phenyl]-acetylamino}-3-chloro-N-(1-ethyl-pyrrolidin-2-ylmethyl)-benzamide | 648.36 | | 212.0 |
| I-44 | 2-[4-Bromo-3-(3-chloro-5-cyano-phenoxy)-2-fluoro-phenyl]-N-[2-chloro-4-(N'-methyl-guanidinocarbonyl)-phenyl]-acetamide | 593.24 | 592 | |
| I-45 | 4-{2-[4-Bromo-3-(3-chloro-5-cyano-phenoxy)-2-fluoro-phenyl]-acetylamino}-3-chloro-N-(1,1-dimethyl-2-pyrrolidin-1-yl-ethyl)-benzamide | 662.38 | | 70.0 |
| I-46 | 2-[4-Bromo-3-(3-chloro-5-cyano-phenoxy)-2-fluoro-phenyl]-N-[2-chloro-4-(N',N'-dimethyl-guanidinocarbonyl)-phenyl]-acetamide | 607.27 | 606 | |
| I-47 | 4-{2-[4-Bromo-3-(3-chloro-5-cyano-phenoxy)-2-fluoro-phenyl]-acetylamino}-3-chloro-N-[2-((R)-2,5-dimethyl-pyrrolidin-1-yl)-ethyl]-benzamide | 662.38 | | 179-181 |
| I-48 | 4-{2-[4-Bromo-3-(3-chloro-5-cyano-phenoxy)-2-fluoro-phenyl]-acetylamino}-3-chloro-N-(4-methyl-piperidin-4-yl)-benzamide; trifluoro-acetic acid salt | 634.33 | | 130.5 |

TABLE I-continued

| Cpd. No. | NAME | mw | ms | mp |
|---|---|---|---|---|
| I-49 | N-(2-Amino-1,1-dimethyl-ethyl)-4-{2-[4-bromo-3-(3-chloro-5-cyano-phenoxy)-2-fluoro-phenyl]-acetylamino}-3-chloro-benzamide; hydrochloride salt | 608.29 | | 158-160.8 |
| I-50 | 4-{2-[4-Bromo-3-(3-chloro-5-cyano-phenoxy)-2-fluoro-phenyl]-acetylamino}-3-chloro-N-(1-methyl-pyrrolidin-3-yl)-benzamide | 620.3 | | 204.0 |
| I-51 | 4-{2-[4-Bromo-3-(3-chloro-5-cyano-phenoxy)-2-fluoro-phenyl]-acetylamino}-3-chloro-N-(1-hydroxymethyl-cyclopropyl)-benzamide | 607.26 | | 247.7-250.1 |
| I-52 | 4-{2-[4-Bromo-3-(3-chloro-5-cyano-phenoxy)-2-fluoro-phenyl]-acetylamino}-3-chloro-N-(3-methyl-1,1-dioxo-tetrahydro-1$\lambda^6$-thiophen-3-yl)-benzamide | 669.35 | | 95-105 |
| I-53 | 4-{2-[4-Bromo-3-(3-chloro-5-cyano-phenoxy)-2-fluoro-phenyl]-acetylamino}-3-chloro-N-(2-methanesulfonyl-ethyl)-benzamide | 643.32 | | 235.5 |
| I-54 | 4-{2-[4-Bromo-3-(3-chloro-5-cyano-phenoxy)-2-fluoro-phenyl]-acetylamino}-3-chloro-N-((3S,4S)-4-hydroxy-1,1-dioxo-tetrahydro-1$\lambda^6$-thiophen-3-yl)-benzamide | 671.33 | | 245 |
| I-55 | 4-{2-[4-Bromo-3-(3-chloro-5-cyano-phenoxy)-2-fluoro-phenyl]-acetylamino}-3-chloro-N-(1,1-dioxo-tetrahydro-1$\lambda^6$-thiophen-3-yl)-benzamide | 655.33 | | 236.6 |
| I-56 | 4-{2-[4-Bromo-3-(3-chloro-5-cyano-phenoxy)-2-fluoro-phenyl]-acetylamino}-3-chloro-N-(1,4-dimethyl-piperidin-4-yl)-benzamide | 648.36 | | 96.0 |
| I-57 | N-(1-Aminomethyl-cyclopropyl)-4-{2-[4-bromo-3-(3-chloro-5-cyano-phenoxy)-2-fluoro-phenyl]-acetylamino}-3-chloro-benzamide; trifluoroacetic acid salt | 606.28 | | 148.0-152.4 |
| I-58 | 4-{2-[4-Bromo-3-(3-chloro-5-cyano-phenoxy)-2-fluoro-phenyl]-acetylamino}-3-chloro-N-(2-hydroxy-1-hydroxymethyl-1-methyl-ethyl)-benzamide | 625.3 | | 69.1 |

[1]Mass spectral data corresponds to the hydrolyzed diol.

Compounds of the present invention can be prepared readily from 3-aryloxy phenylacetic acids 10b. The appropriate phenylacetic acid compound is converted to the corresponding acid chloride 10c and condensed with an optionally substituted 4-amino-benzoic acid ester 11. After hydrolysis of the ester the resulting carboxylic acid 12b is activated and treated with a primary or secondary amine to afford the desired amide 13.

SCHEME 1

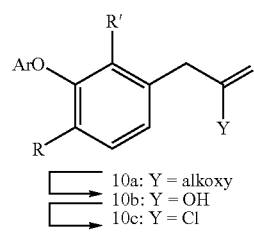

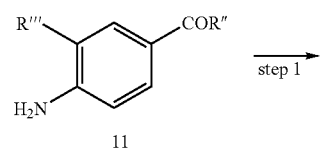

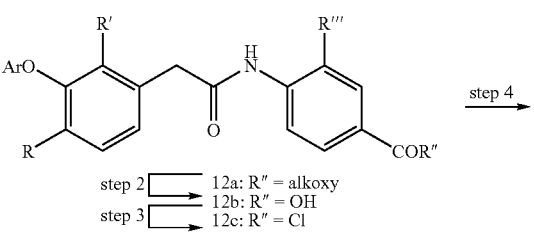

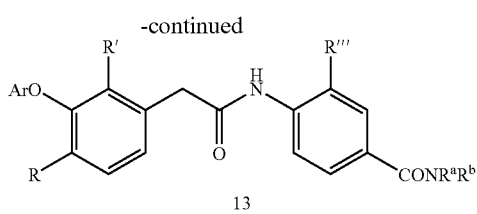

Ar = phenyl substituted with halogen, cyano, haloalkyl, alkyl, cycloalkyl
R = halogen, alkyl, alkoxy
R' = hydrogen or fluoro
R'' = hydrogen, alkyl, halogen or an activating group
R''' = hydrogen, halogen or alkyl 3-Aryloxy-2-fluoro-4-substituted-phenylacetic acid esters (10a, R=halogen or alkyl, R'=fluoro) compounds were accessible by exploiting the facile displacement of fluorine atoms from fluoroaromatic compounds. Treatment of 1,2,3-trifluoro-4-nitro-benzene (15) with an alkali metal phenolate results in displacement of the 3-fluoro group with good regioselectivity to afford 16a (SCHEME 2). Treatment of 16a with carbanion formed by deprotonation of tert-butyl ethyl malonate results in the regioselective introduction of a malonic ester (16b) which is subjected to acid-catalyzed hydrolysis of the tert-butyl ester and decarboxylation to afford 16c. After introduction of the phenoxy and acetic acid (or acetonitrile) moieties, the nitro group is readily converted to other substituents at the 4-position. Reduction of the nitro substituent afforded 17a which was subjected to Sandmeyer conditions to introduce a bromo 17b or chloro 17e substituent. Optionally the bromo substituent was further reacted with a dialkyl zinc (the Negishi coupling) to afford 4-alkyl-3-aryloxy-2-fluoro-phenylacetic acid compounds exemplified by 17c and 17d.

The Negishi coupling of organozinc halides or dialkylzinc with haloarenes and aryl triflates is an effective means for attachment of an alkyl group to an arene. The reaction is catalyzed by palladium Pd(0) and palladium is preferably ligated to a bidentate ligand including Pd(dppf)Cl$_2$ and Pd(dppe)Cl$_2$. (J. M. Herbert *Tetrahedron Lett.* 2004 45:817-819) Typically the reaction is run an inert aprotic solvent and common ethereal solvents include dioxane, DME and THF are suitable. The reaction is commonly run at elevated temperature.

The requisite phenols utilized in the condensation with 15 or 18b were prepared as depicted in SCHEME 3. Dibromofluorobenzene (20a) was treated with sodium methoxide resulting in displacement of the fluorine substituent to afford 20b. Monometallation and formylation of the resulting lithium salt with DMF afforded 21. Conversion of the formyl group into a difluoromethyl group was effected with DAST. Demethylation of the methyl ether afforded the requisite phenol 23. 3-Chloro-5-hydroxy-benzonitrile (24c) was prepared form 3,5-dichloro-benzonitrile by displacement of a chlorine substitutent with sodium methoxide and demethylation of the resulting ether to afford 24c.

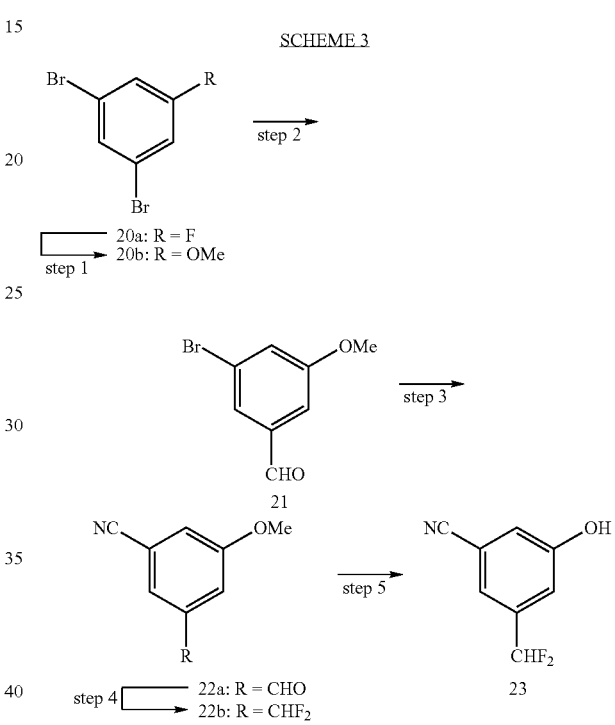

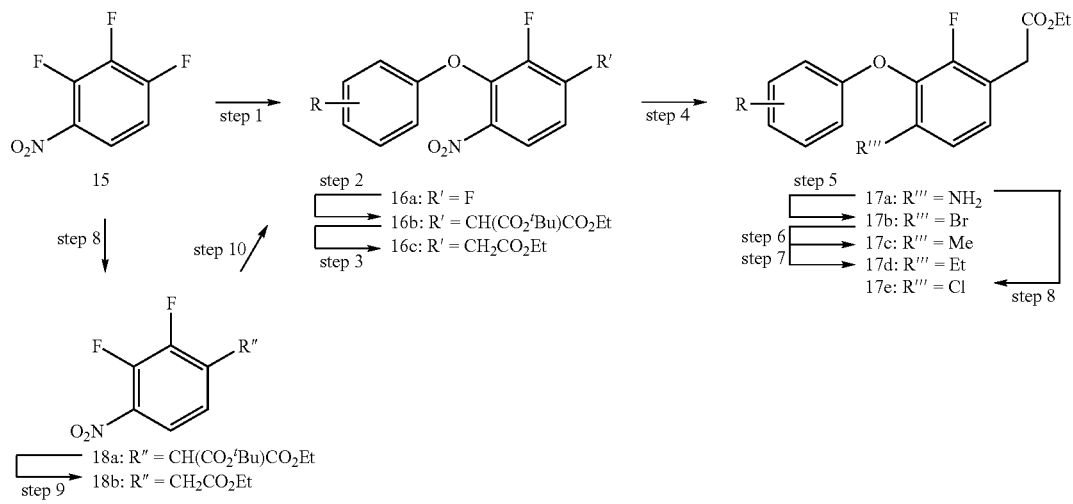

-continued

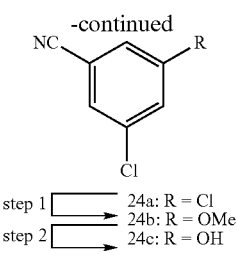

step 1 [ 24a: R = Cl
         24b: R = OMe
step 2 [ 24c: R = OH

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH or LiOH (in approximately a 10% molar excess) at room temperature for about 30 minutes. The solvent is removed and the residue taken up in an organic solvent such as diethyl ether, treated with a dialkyl formamide and an excess of oxalyl chloride. This is all affected at a moderately reduced temperature between about −10 to 10° degrees C. The resulting solution is then stirred at the reduced temperature for 1-4 hours. Solvent removal provides a residue which is taken up in an inert organic solvent s e.g. DCM, EtOAc, THF or toluene, cooled to about 0° C. and treated with concentrated ammonium hydroxide or an appropriate amine. Excess amine must be provided as the reaction produces HCl which forms a non-reactive ammonium salt. Alternatively a trialkyl amine or pyridine is incorporated in the reaction as a base to react with the HCl formed during the reaction. The resulting mixture is stirred at a reduced temperature for 1-4 hours. Alternatively one skilled in the art will appreciate that the amidation of an acyl halide can be carried out in an aqueous organic solvent in the presence of an alkali metal carbonate and the appropriate amine (Schotten-Bauman conditions)

Alternatively the acid may be activated with 1 equivalent of a suitable coupling agent or dehydrating agent, e.g., 1-[3-(dimethylamino)propyl]-3-ethylcarbodiimide hydrochloride, CDI (1,1'-carbonyidiimidazole) or DCC (1,3-dicyclohexylcarbodiimide). Numerous additives have been identified which improve the coupling efficiency including, 1-hydroxybenzotriazole and 3-hydroxy-3,4-dihydro-4-oxo-1,2,3-benzotriazine (W. König and R. Geiger *Chem. Ber.* 1970 788:2024 and 2034), N-hydroxysuccinimide (E. Wunsch and F. Drees, *Chem. Ber.* 1966 99:110), 1-hydroxy-7-azabenzotriazole (L. A. Carpino *J. Am. Chem. Soc.* 1993 115:4397-4398). Protocols for dehydrative coupling have been extensively refined in the peptide synthesis art and these protocols can be used herein. These protocols have been reviewed, see e.g., M. Bodanszky, *Principles of Peptide Synthesis*, Springer Verlag, New York 1993; P. Lloyd-Williams and F. Albericio *Chemical Methods for the Synthesis of Peptides and Proteins* CRC Press, Boca Raton, Fla. 1997.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor other wise undesirable, and includes excipients that are acceptable for veterinary use as well as human pharmaceutical use. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. N-acylsulfonamides have an acidic proton which can be abstracted to form a salt with an organic or inorganic cation.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The status of an HIV infection can be monitored by measuring viral load (RNA) or monitoring T-cell levels. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another non-nucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, treatment of a HIV-1 infection, as used herein, also includes treatment or prophylaxis of a disease or a condition associated with or mediated by HIV-1 infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

These examples and preparations which follow are provided to enable those skilled in the art to more clearly understand and to practice the present invention. They should not be considered as limiting the scope of the invention, but merely as being illustrative and representative thereof.

EXAMPLE 1

4-{2-[4-Bromo-3-(3-chloro-5-cyano-phenoxy)-2-fluoro-phenyl]-acetylamino}-3-chloro-N-(2-pyrrolidin-1-yl-ethyl)-benzamide (I-32)

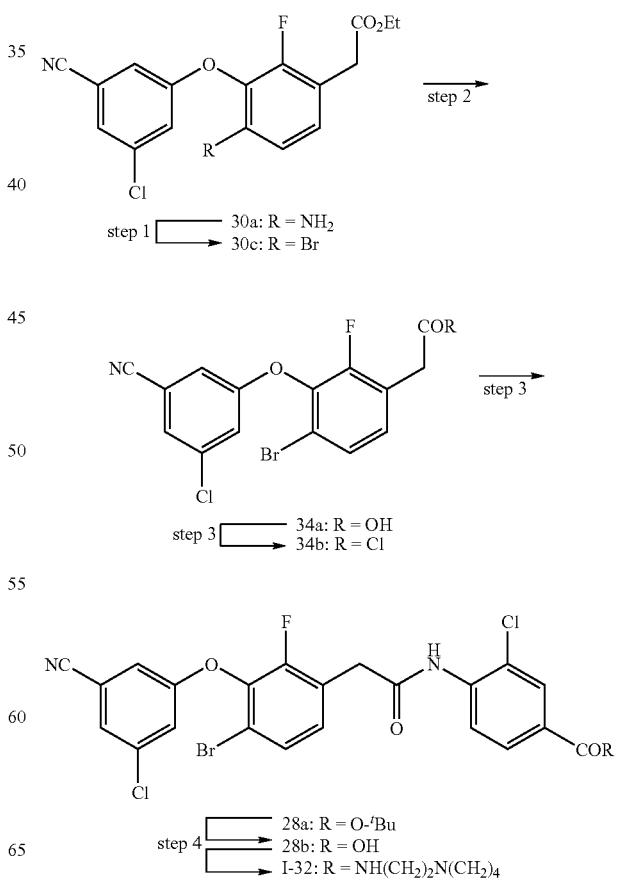

-continued

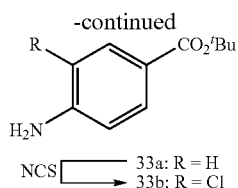

33a: R = H
33b: R = Cl

The phenyl acetic acid 30a was prepared as described in example 3.

step 1—A 150 mL three-neck round bottom flask was charged with MeCN (50 mL), CuBr (2.8 g, 12.61 mmol) and t-butyl nitrite (1.4 g, 13.76 mmol), degassed and maintained under an Ar atmosphere and heated to 70° C. To the mixture was added dropwise a solution of 30a (4.0 g, 11.47 mmol) dissolved MeCN (20 mL). The reaction mixture was stirred at 70° C for 4 h and then cooled to 0° C. The reaction was quenched by addition of 10 % HCl (30 mL) and extracted with EtOAc. The combined extracts were sequentially washed with 10% HCl and brine. The organic extract was dried ($Na_2SO_4$), filtered and the volatile solvents removed in vacuo to yield a black oil which was purified by flash chromatography on silica gel (hexanes:EtOAc 95:5) to afford 2.5 g (52.8% theory) of 30c.

Step 2 was carried out as described in step 8 of example 3 except 30c was used in place of 30b which afforded the carboxylic acid 34a.

step 3—DMF (1 drop) was added to a solution of 34a (0.78 g, 2.0 mmol) and oxalyl chloride (0.34 mL, 2 equiv) in DCM (5 mL). The solution was stirred for 2 h, and the volatile materials were removed under vacuum. The resulting acid chloride 34b was dissolved in dry DCM (3 mL), and added dropwise to a solution of 33b (0.46 g, 1 equiv) in dry pyridine (3 mL). The solution was stirred for 36 h, poured into water, and extracted with ether. The combined organics were washed with 0.5 M HCl solution, water, and brine. Evaporation of the volatile materials and purification of the residue by $SiO_2$ chromatography eluting with an EtOAc/hexane gradient (0% to 25% EtOAc) afforded 0.57 g (48%) of 28a.

step 4—A solution of 28a (0.57 g, 0.97 mmol) and formic acid (5 mL) was stirred for 2 h. The reaction was then heated to 35° C. for 3 h and cooled to RT. The heterogeneous solution was filtered and the collected solid was dried in vacuo to afford 0.34 g (65%) of 28b which was used without additional purification. To a solution of 28b (0.20 g, 0.37 mmol), DMF (1.5 mL) and DCM (4 mL) was added HOBT (0.085 g, 1.5 equiv) and EDCI supported on resin (0.52 g, 2 equiv). The solution was stirred for 12 h then DIPEA and 2-pyrrolidin-1-yl-ethylamine were added, and the solution was stirred for 24 h. DMF (3 mL) was added to the reaction mixture, and the solution was filtered, washing with methylene chloride. The solvents were removed, and the residue was purified by $SiO_2$ chromatography eluting with a DCM/DCM:MeOH:$NH_4$Cl gradient (0% to 80% of the DCM/MeOH solution) to afford 0.10 g(42%) of I-33 as a white solid.

4-Amino-3-chloro-benzoic acid, tert-butyl ester (33b)—NCS (3.63 g, 1.05 equiv) was added in one portion to a solution of tert-butyl-4-amino-benzoate (33a, 5 g, 25.8 mmol) in a mixture of IPA (52 mL) and MeCN (52 mL) at 60° C. The resulting mixture was heated to 80° C. for 1 h and concentrated under vacuum. The residue was dissolved in DCM and washed with 1M NaOH and brine. The organic extracts were concentrated and purified by $SiO_2$ chromatography eluting with an EtOAc/hexane gradient (0% to 20% EtOAc) to afford 4.9 g (83%) of 33b as red oil that slowly solidified.

4-{2-[4-Bromo-3-(3-chloro-5-cyano-phenoxy)-2-fluoro-phenyl]-acetylamino}-3-chloro-N-(3-methyl-1,1-dioxo-tetrahydro-1$\lambda^6$-thiophen-3-yl)-benzamide (I-52) was prepared analogously except in step 4, 2-pyrrolidin-1-yl-ethylamine was replaced with 3-methyl-1,1-dioxo-tetrahydro-1$\lambda^6$-thiophen-3-ylamine (CAS Reg. No 151775-02-9, available from Matrix Scientific, Columbia, S.C.).

4-{2-[4-Bromo-3-(3-chloro-5-cyano-phenoxy)-2-fluoro-phenyl]-acetylamino}-3-chloro-N-((3S,4S)-4-hydroxy-1,1-dioxo-tetrahydro-1$\lambda^6$-thiophen-3-yl)-benzamide (I-54) was prepared analogously except in step 4, 2-pyrrolidin-1-yl-ethylamine was replaced with (3S,4S)-4-amino-1,1-dioxo-tetrahydro-1$\lambda^6$-thiophen-3-ol (W. R. Sorenson, *J. Org. Chem.* 1959 29:1796, CAS Reg. No. 55261-00-2)

4-{2-[4-Bromo-3-(3-chloro-5-cyano-phenoxy)-2-fluoro-phenyl]-acetylamino}-3-chloro-N-(1,1dioxo-tetrahydro-1$\lambda^6$-thiophen-3-yl)-benzamide (I-55) was prepared analogously except in step 4, 2-pyrrolidin-1-yl-ethylamine was replaced with 1,1-dioxo-tetrahydro-1$\lambda^6$-thiophen-3-ylamine (S. M. Liebowitz et al., *Biochem. Pharmacol.* 1989 38(3): 399-406, CAS Reg. No. 6338-70-1).

4-{2-[4-Bromo-3-(3-chloro-5-cyano-phenoxy)-2-fluoro-phenyl]-acetylamino}-3-chloro-N-(2-methanesulfonyl-ethyl)-benzamide (I-53) was prepared analogously except in step 4, 2-pyrrolidin-1-yl-ethylamine was replaced with 2-methanesulfonyl-ethylamine (Liebowitz, supra, CAS Reg. No. 49773-20-8)

EXAMPLE 2

4-{2-[4-Bromo-3-(3-chloro-5-cyano-phenoxy)-2-fluoro-phenyl]-acetylamino}-3-methyl-N-(2-pyrrolidin-1-yl-ethyl)-benzamide (I-27)

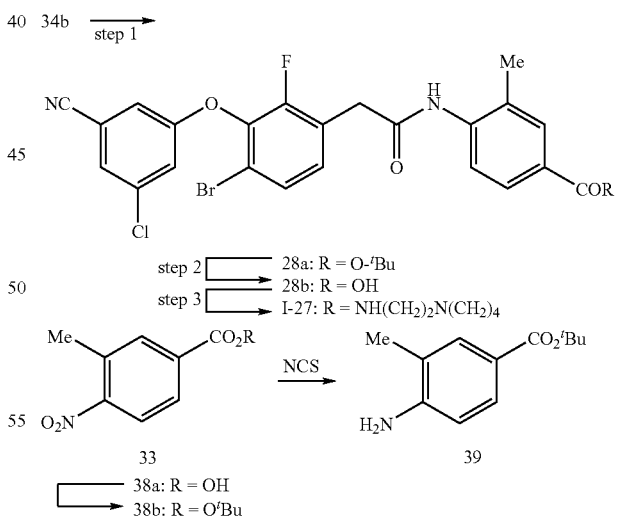

28a: R = O-$^t$Bu
28b: R = OH
I-27: R = NH(CH$_2$)$_2$N(CH$_2$)$_4$

38a: R = OH
38b: R = O$^t$Bu

4-Amino-3-methyl-benzoic acid, tert-butyl ester—Benzene sulfonyl chloride (12.8 mL, 1 equiv) was added to a solution 38a (18.1 g, 99 mmol) in pyridine (200 mL). The solution was stirred for 15 min, and tert-butyl alcohol (9.4 mL, 1 equiv) was added dropwise. After 1.5 h, the solution was poured into 400 mL of ice-water and stirred for 1 h. The solution was filtered, and the solvent was collected and dried under vacuum. This material was dissolved in toluene and passed through a plug of silica to provide, after evaporation of the volatile materials, 6.6 g (28%) of 38b.

A suspension of 38b (6.6 g, 27 mmol) and 10% Pd/C (0.55 g) in EtOH (200 mL) was agitated under $H_2$ (60 psi) for 3 h. The solution was filtered through CELITE®, and the volatile materials were evaporated to afford 5.7 g (99%) of 39 as an oil that slowly solidified.

step 1—The acid chloride 34b (0.66 g, 2.0 mmol) was prepared as described in step 3 of example 1. A solution of 34b and acetone (3 mL) was added to a suspension of NaHCO$_3$ (0.34 g, 2 equiv) and 39. The solvent was removed, and the residue was partitioned between EtOAc and water. The aqueous layer was extracted with EtOAc, and the combined organic layers were dried, filtered, and concentrated. The resulting yellow oil was purified by SiO$_2$ chromatography eluting with 30% EtOAc/hexanes to afford 1.1 g (100%) of 28a as a yellow solid.

Steps 2 and 3 were carried out as described for step 4 of example 1to afford I27. 4-{2-[4-Bromo-3-(3-chloro-5-cyano-phenoxy)-2-fluoro-phenyl]-acetylamino}-N-[2-(1,1-dioxo-1$\lambda^6$-thiomorpholin-4-yl)-ethyl]-3-methyl-benzamide (I-24) was prepared by the procedure described in steps 1 to 3 of example 2 except in step 3, 2-(1,1,-dioxo-1$\lambda^6$-thiomorpholin-4-yl)-ethylamine was used in place of aminoethylpyrrolidine.

4-{2-[4-Bromo-3-(3-chloro-5-cyano-phenoxy)-2-fluoro-phenyl]-acetylamino}-N-[2-(4-hydroxy-piperidin-1-yl)-ethyl]-3-methyl-benzamide (I-25) was prepared by the procedure described in steps 1 to 3 of example 2 except in step 3, 1-(2-amino-ethyl)-piperidin-4-ol was used in place of aminoethylpyrrolidine.

4-{2-[4-Bromo-3-(3-chloro-5-cyano-phenoxy)-2-fluoro-phenyl]-acetylamino}-N-(2-dimethylamino-1-methyl-ethyl)-3-methyl-benzamide (I-26) was prepared by the procedure described in steps 1 to 3 of example 2 except in step 3, N$^1$,N$^1$-dimethyl-propane-1,2-diamine was used in place of aminoethylpyrrolidine.

4-{2-[4-Bromo-3-(3-chloro-5-cyano-phenoxy)-2-fluoro-phenyl]-acetylamino}-3-methyl-N-(2morpholin-4-yl-ethyl)-benzamide (I-28) was prepared by the procedure described in steps 1 to 3 of example 2 except in step 3, 2-morpholin-4-yl-ethylamine was used in place of aminoethylpyrrolidine.

N-(2-Amino-ethyl)-4-{2-[4-chloro-3-(3-chloro-5-cyano-phenoxy)-2-fluoro-phenyl]-acetylamino}-3-methyl-benzamide (I-29) was prepared by the procedure described in steps 1 to 3 of example 2 except in step 3, (2-amino-ethyl)-carbamic acid, tert-butyl ester was used in place of aminoethylpyrrolidine.

42

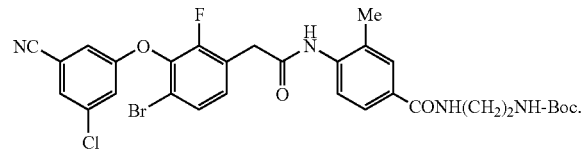

The Boc-protecting group was removed by adding TFA (1.5 mL) to a solution of the carbamate 42 (0.27 g, 0.43 mmol) and DCM (5 mL) cooled to 0° C. The solution was warmed to RT and stirred for 1 h. The volatile materials were removed. The residue was dissolved in DCM, and the organics were washed with saturated NH$_4$OH. A precipitate formed which was collected by filtration to afford 0.086 g (39%) of I29.

4-{2-[4-Bromo-3-(3-chloro-5-cyano-phenoxy)-2-fluoro-phenyl]-acetylamino}-3-methyl-N-(2-piperazin-1-yl-ethyl)-benzamide (I-30) was prepared by the procedure described in steps 1 to 3 of example 2 except in step 3, 2-piperazin-1-yl-ethylamine was used in place of aminoethylpyrrolidine.

4-{2-[4-Bromo-3-(3-chloro-5-cyano-phenoxy)-2-fluoro-phenyl]-acetylamino}-3-methyl-N-pyrrolidin-3-yl-benzamide (I-31) was prepared by the procedure described in steps 1 to 3 of example 2 except in step 3, 3-amino-pyrrolidine was used in place of aminoethylpyrrolidine.

4-{2-[4-Bromo-3-(3-chloro-5-cyano-phenoxy)-2-fluoro-phenyl]-acetylamino}-3-chloro-N-2-(4,4-difluoro-piperidin-1-yl)-ethyl]-benzamide; hydrochloride salt (I-40) was prepared by the procedure described in steps 1 to 3 of example 2 except in step 3, 2-(4,4-difluoro-piperidin-1-yl)-ethylamine (CAS Reg. No 605659-03-8, Oakwood Products Inc, West Columbia S.C.) was used in place of aminoethylpyrrolidine.

N-{2-[Bis-(2-hydroxy-ethyl)-amino]-ethyl}-4-{2-[4-bromo-3-(3-chloro-5-cyano-phenoxy)-2-fluoro-phenyl]-acetylamino}-3-chloro-benzamide (I-41) was prepared by the procedure described in steps 1 to 3 of example 2 except in step 3, 2,2'-[(2-aminoethyl)imino]bis-ethanol (C. A. Potter et al. WO00/38734, CAS Reg. No 3197-06-6) was used in place of aminoethylpyrrolidine.

4-{2-[4-Bromo-3-(3-chloro-5-cyano-phenoxy)-2-fluoro-phenyl]-acetylamino}-3-chloro-N-(2-dimethylamino-1-methyl-ethyl)-benzamide (I-42) was prepared by the procedure described in steps 1 to 3 of example 2 except in step 3, N$^1$,N$^1$-dimethyl-propane-1,2-diamine (N. Vicker et al., *J. Med. Chem.* 2002 45:721, CAS Reg. No. 70831-55-9) was used in place of aminoethylpyrrolidine.

4-{2-[4-Bromo-3-(3-chloro-5-cyano-phenoxy)-2-fluoro-phenyl]-acetylamino}-3-chloro-N-(1-ethyl-pyrrolidin-2-yl-methyl)-benzamide (I-43) was prepared by the procedure described in steps 1 to 3 of example 2 except in step 3, C-(1-ethyl-pyrrolidin-2-yl)-methylamine (J. E. Biskop et al., *J. Med. Chem.* 1991 34(5):1612, CAS Reg No. 69500-64-7) was used in place of aminoethylpyrrolidine.

4-{2-[4-Bromo-3-(3-chloro-5-cyano-phenoxy)-2-fluoro-phenyl]-acetylamino}-3 -chloro-N-(1,1-dimethyl-2-pyrrolidin-1-yl-ethyl)-benzamide (I-45) was prepared by the procedure described in steps 1 to 3 of example 2 except in step 3, 1, 1-dimethyl-2-pyrrolidin-1-yl-ethylamine (S. Schutz et al. *Arzneim. Forsch.* 1971 21(6):739-763, CAS Reg. No. 34155-39-0) was used in place of aminoethylpyrrolidine.

4-{2-[4-Bromo-3-(3-chloro-5-cyano-phenoxy)-2-fluoro-phenyl]-acetylamino}-3-chloro -N-[2-((R)-2,5-dimethyl-pyrrolidin-1-yl)-ethyl]-benzamide (I-47) was prepared by the procedure described in steps 1 to 3 of example 2 except in step 3, 2-((2R,5R)-2,5-dimethyl-pyrrolidin-1-yl)-ethylamine (J. Bock et al. *Arzneim. Forsch.* 1971 21(12):2089-2100, CAS Reg. No. 33304-27-7) was used in place of aminoethylpyrrolidine.

4-{2-[4-Bromo-3-(3-chloro-5-cyano-phenoxy)-2-fluoro-phenyl]-acetylamino}-3-chloro-N-(1-methyl-pyrrolidin-3-yl)-benzamide (I-50) was prepared by the procedure described in steps 1 to 3 of example 2 except in step 3, 1-methyl-pyrrolidin-3-ylamine (M. Allegretti et al. *J. Med Chem.* 2002 48:4312-4331, CAS Reg. No. 13220-33-2) was used in place of aminoethylpyrrolidine.

4-{2-[4-Bromo-3-(3-chloro-5-cyano-phenoxy)-2-fluoro-phenyl]-acetylamino}-3-chloro-N-(1,4-dimethyl-piperidin-4-yl)-benzamide (I-56) was prepared by the procedure described in steps 1 to 3 of example 2 except in step 3, 1,4-dimethyl-piperidin-4-ylamine 52 was used in place of aminoethylpyrrolidine. 1,4-Dimethyl-piperidin-4-ylamine is prepared from 1-benzyl-4-methyl-piperidin-4-ylamine (F.

Himmelsbach et al. U.S. Pat. No.5,821,240) by conversion of the amine to a tert-butoxycarbonylamino, substituent, hydrogenolysis of the benzyl group, reductive methylation of the piperidine nitrogen with formaldehyde and NaBH(OAc)$_3$ and removal of the Boc protecting group.

4-{2-[4-Bromo-3-(3-chloro-5-cyano-phenoxy)-2-fluoro-phenyl]-acetylamino}-3-chloro-N-(4-methyl-piperidin-4-yl)-benzamide; trifluoro-acetic acid salt (1-48) was prepared by the procedure described in steps 1 to 3 of example 2 except in step 3, 1-benzyl-4-methyl-piperidin-4-ylamine was used in place of aminoethylpyrrolidine and the benzyl substituent is removed by catalytic hydrogenolysis.

N-(2-Amino-1,1-dimethyl-ethyl)-4-{2-[4-bromo-3-(3-chloro-5-cyano-phenoxy)-2-fluoro-phenyl]-acetylamino}-3-chloro-benzamide; hydrochloride salt (I-49) was prepared by the procedure described in steps 1 to 3 of example 2 except in step 3, (2-amino-1,1-dimethyl-ethyl)-carbamic acid tert-butyl ester (M. Pittelkow et al., *Synthesis* 2002 15:2195-2202) was used in place of aminoethylpyrrolidine and the Boc group is removed as described above.

EXAMPLE 3

3-Chloro-4-{2-[4-chloro-3-(3-chloro-5-cyano-phenoxy)-2-fluoro-phenyl]-acetylamino}-N-(2-dimethylamino-ethyl)-benzamide (I-21)

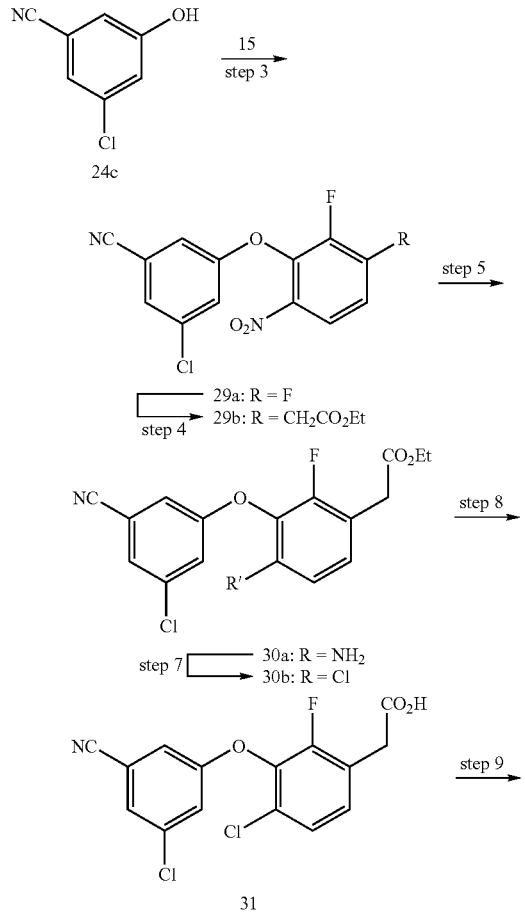

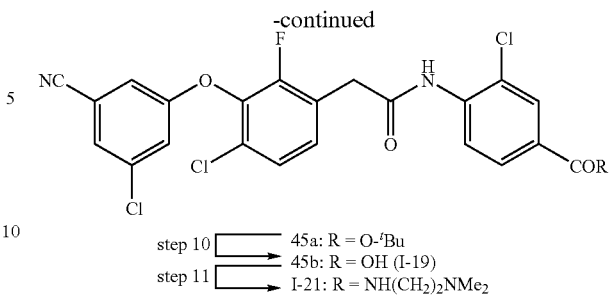

Steps 1 and 2 are depicted in Scheme 3 step 1—A 100 ml round bottom flask was charged under a stream of nitrogen with 3,5-dichlorobenzonitrile (24a, 7.0 g, 40.69 mmol) and anhydrous DMF (75 mL). To the solution was added sodium methoxide (2.26 g, 44.76 mmol) and resulting solution was stirred further at RT for 24 h. When the reaction was complete, aqueous 10% hydrochloric acid added dropwise to the reaction vessel. The crude mixture was extracted with EtOAc and sequentially washed with aqueous acid, water and brine. The EtOAc extracts were dried (Na$_2$SO$_4$), filtered and the solvent was removed in vacuo to afford a crude solid which was recrystallized from hexane/acetone to afford 5.9 g (86%) of 24b.

step 2—A 250 mL flask was charged with 24b (7.0 g, 41.766 mmol) and 2,4,6-collidine (100 mL). The mixture was heated to 170° C. and LiI (16.76 g, 125.298 mmol) was added and the reaction mixture was heated for 4 h. When 24b was consumed the reaction was cooled to RT and quenched with 10% aqueous HCl. The resulting mixture was extracted with EtOAc and washed with water and brine. The EtOAc extract was dried over (Na$_2$SO$_4$) and filtered. The solvent was removed in vacuo to afford a yellow oil which was purified by silica gel chromatography eluting with EtOAc/hexane (10:90) to afford 6.0 g (94%) of 24c.

step 3—A 250 mL round-bottom flask was charged with 24c (6.0 g, 39.070 mmol) and anhydrous THF (100 mL) and the solution was cooled to 0° C. To the cooled solution was added sodium tert-butoxide (46.89 g, 4.51 mmol) and the resulting solution stirred for 1 h. 2,3,4-Trifluoro-nitro-benzene (15, 6.92 g, 39.070 mmol) was added dropwise while maintaining the reaction at 0° C. until phenol was completely consumed. The mixture was quenched by addition of 10% aqueous HCl and the resulting mixture was stirred for an additional hour. The mixture was extracted with EtOAc and washed with water and brine. The EtOAc was dried (Na$_2$SO$_4$) and filtered. The solvent was removed in vacuo to yield a yellow oil which was purified by SiO$_2$ column chromatography eluting with hexane/EtOAc (92:8) to afford 10 g (82%) of 29a.

step 4—A solution of tert-butyl ethyl malonate (10.31 g, 54.80 mmol) and anhydrous NMP (200 mL) cooled to 0° C. and stirred under a nitrogen atmosphere. To this solution was added NaH 40% in mineral oil (1.84 g, 76.70 mmol). The mixture was allowed to stir at 0° C. for an additional 1 h. The bis-aryl ether 29a (15.00 g, 49.80 mmol) was then added to the reaction vessel and stirred under nitrogen at RT until the reaction was complete. The mixture was quenched by addition of aqueous 10% HCl at RT. The mixture was extracted with EtOAc and washed with water and brine. The EtOAc was dried (Na$_2$SO$_4$) and filtered. The solvent was removed in vacuo to the malonate diester adduct as a light yellow oil which was used without any further purification.

The diester (24.0 g, 50.117 mmol) was dissolved in dichloroethane (300 mL) and TFA (6.29 g, 55.13 mmol) and heated to 75° C. for 24 h. The mixture was cooled to RT and solvent and excess TFA were removed in vacuo. The crude oil was re-dissolved in DCM and cooled to 0° C. and aqueous NaHCO$_3$ was added. The mixture was extracted with DCM and washed with water and brine. The DCM was dried (Na$_2$SO$_4$), filtered and the solvent was removed in vacuo to afford a yellow oil. The crude oil was purified by SiO$_2$ chromatography eluting with hexane/EtOAc (90:10) to afford 15.0 g (80%) of 29b.

step 6—A 250 mL round bottom flask was charged with 29b (8.0, 21.12 mmol) and absolute EtOH. To the reaction vessel was added ammonium chloride (2.26 g, 42.244 mmol), water (30 mL) and iron (1.17 g, 21.12 mmol). The reaction was stirred and heated to 80° C. for 4 h. When 29b was consumed, the hetergogeneous mixture was filtered through a pad of CELITE® and the filter cake was washed with EtOAc. The aqueous filtrate was extracted with EtOAc and washed with water and brine. The combined EtOAc extracts were dried over (Na$_2$SO$_4$) and filtered. The solvent was removed in vacuo to afford a pale oil which was purified by SiO$_2$ chromatography eluting with hexane/EtOAc (85:15) to afford 6.0 g (87%) of 30a.

step 7—A 100 mL round bottom flask was charged with anhydrous MeCN (15 mL) under a continuous stream of nitrogen. To this mixture was added Cu(II)Cl$_2$ (0.083 g, 0.624 mmol) and tert-butyl nitrite (0.064 g, 0.624 mmol). The mixture was heated to 70° C. for 30 min. To this mixture was added 30a (0.100 g, 0.624 mmol) in a single portion and stirring was continued for an additional 2 h. Upon consumption of starting materials the mixture was cooled to RT and the reaction mixture was quenched with aqueous 10% HCl. The mixture was extracted with EtOAc and the combined extracts were washed with water and brine. The EtOAc extract was dried (Na$_2$SO$_4$) and filtered. The solvent was removed in vacuo to afford a light brown oil which was purified by SiO$_2$ chromatography eluting with hexane/EtOAc (96:4) to afford 0.080 g (76%) of 30b.

step 8—A dried 100 mL round bottom flask purged with nitrogen and charged with 30b (2.0 g; 5.43 mmol) and dissolved in THF (20 mL) and stirred under a stream of nitrogen. To the reaction vessel was added LiOH (0.46 g; 10.86 mmol) followed by 5 mL deionized water. The reaction was stirred for 1 h under a continuous stream of nitrogen. The homogeneous mixture was quenched at 0° C. with 10% aqueous HCl. The reaction mixture was stirred for an additional 15 minutes. The crude mixture was extracted with EtOAc and washed with water and brine. The organic extracts were dried (Na$_2$SO$_4$) and filtered. The solvent was removed in vacuo and the crude acid 31 was used without any further purification.

Steps 9 to 11 were carried out as described for steps 3 and 4 of example 1 except in step 4, N$^1$-N$^1$-dimethyl-ethane-1,2-diamine was used in place of 2-pyrrolidin-1-yl-ethylamine to afford I21.

4-{2-[4-bromo-3-(3-chloro-5-cyano-phenoxy)-2-fluoro-phenyl]-acetylamino}-3-methyl-benzoic acid (I-22) was prepared as described in steps 1-10 of example 3 except in step 9, 4-amino 3-methyl-benzoic acid, tert-butyl ester (39) was used in place of 4-amino 3-chloro-benzoic acid, tert-butyl ester 33b and the acylation procedure in step 1 of example 2 was utilized.

4-{2-[4-Chloro-3-(3-chloro-5-cyano-phenoxy)-2-fluoro-phenyl]-acetylamino}-3-methyl-N-(2-methylamino-ethyl)-benzamide (I-23) was prepared from I-22 using the procedure of step 4 of example 1 except aminoethylpyrrolidine was replaced with N-methyl-ethane-1,2-diamine and the acylation procedure in step 1 of example 2 was utilized.

4-{2-[4-Chloro-3-(3-chloro-5-cyano-phenoxy)-2-fluoro-phenyl]-acetylamino}-3-methyl-benzamide (I-2) was prepared by the procedure described in Example 3 except in step 9, 4-amino-3-methyl-benzamide was used in place of 33b and the acylation procedure in step 1 of example 2 was utilized. 4-amino-3-methyl-benzamide was prepared by hydrogenation of an ethanolic solution of 3-methyl-4-nitro-benzamide with 10% Pd/C as the catalyst.

4-{2-[4-Chloro-3-(3-chloro-5-cyano-phenoxy)-2-fluoro-phenyl]-acetylamino}-3-methyl-benzoic acid (I-3) was prepared by the procedure described in steps 1 to 10 of example 3 except in step 9, 4-amino 3-methyl-benzoic acid, tert-butyl ester (39) was used in place of 4-amino 3-chloro-benzoic acid, tert-butyl ester 33b and the acylation procedure in step 1 of example 2 was utilized.

4-{2-[4-Chloro-3-(3-chloro-5-cyano-phenoxy)-2-fluoro-phenyl]-acetylamino}-N-(2-dimethylamino-ethyl)-3-methyl-benzamide (I-4) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b and the acylation procedure in step 1 of example 2 was utilized. 4-{2-[4-Chloro-3-(3-chloro-5-cyano-phenoxy)-2-fluoro-phenyl]-acetylamino}-N-(2-dimethylamino-ethyl)-3-methyl-benzamide trifluoro-acetate salt (I-5) was obtained from the purification of I4 by reverse phase HPLC eluting with TFA/H$_2$O/MeCN.

2-[4-Chloro-3-(3-chloro-5-cyano-phenoxy)-2-fluoro-phenyl]-N-[2-methyl-4-(4-methyl-piperazine-1-carbonyl)-phenyl]-acetamide trifluoro-acetate salt (I-6) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b and the acylation procedure in step 1 of example 2 was utilized and in step 11, 1-methyl-piperazine was used in place of N$^1$-N$^1$-dimethyl-ethane-1,2-diamine. The trifluoroacetic acid salt was prepared as described for I-5.

2-[4-Chloro-3-(3-chloro-5-cyano-phenoxy)-2-fluoro-phenyl]-N-[4-(( R)-3-hydroxy-pyrrolidine-1-carbonyl)-2-methyl-phenyl]-acetamide (I-7) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, (R)-3-hydroxy-pyrrolidine was used in place of 2- N$^1$-N$^1$-dimethyl-ethane-1,2-diamine.

4-{2-[4-Chloro-3-(3-chloro-5-cyano-phenoxy)-2-fluoro-phenyl]-acetylamino}-N-(2-hydroxy-ethyl)-3-methyl-benzamide (I-8) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, 2-amino-ethanol was used in place of N$^1$-N$^1$-dimethyl-ethane-1,2-diamine.

4-{2-[4-Chloro-3-(3-chloro-5-cyano-phenoxy)-2-fluoro-phenyl]-acetylamino}-3-methyl-N-(4-methyl-piperazin-1-yl)-benzamide; compound with trifluoro-acetic acid (I-9) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, 4-methyl-piperazin-1-ylamine was used in place of N$^1$-N$^1$-dimethylethane-1,2-diamine. The product was converted to the trifluoroacetate salt as described for I5.

4-{2-[4-Chloro-3-(3-chloro-5-cyano-phenoxy)-2-fluoro-phenyl]-acetylamino}-N-((R)-2-hydroxy-propyl)-3-methyl-benzamide (I-10) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, (R)-1-amino-propan-2-ol was used in place of $N^1$-$N^1$-dimethyl-ethane-1,2-diamine.

2-[4-Chloro-3-(3-chloro-5-cyano-phenoxy)-2-fluoro-phenyl]-N-[4-(4-hydroxy-piperidine-1-carbonyl)-2-methyl-phenyl]-acetamide (I-11) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, 4-hydroxy-piperidine was used in place of $N^1$-$N^1$-dimethyl-ethane-1,2-diamine.

2-[4-Chloro-3-(3-chloro-5-cyano-phenoxy)-2-fluoro-phenyl]-N-[2-methyl-4-(morpholine-4-carbonyl)-phenyl]-acetamide (I-12) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, 4-morpholine was used in place of $N^1$-$N^1$-dimethyl-ethane-1,2-diamine.

4-{2-[4-Chloro-3-(3-chloro-5-cyano-phenoxy)-2-fluoro-phenyl]-acetylamino}-3-methyl-N-pyridin-4-ylmethyl-benzamide; trifluoro-acetate salt (I-13) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, 4-aminomethyl-pyridine was used in place of $N^1$-$N^1$-dimethyl-ethane-1,2-diamine. The product was converted to the trifluoroacetate salt as described for I-5.

4-{2-[4-Chloro-3-(3-chloro-5-cyano-phenoxy)-2-fluoro-phenyl]-acetylamino}-3-methyl-N-(2-pyrrolidin-1-yl-ethyl)-benzamide; trifluoro-acetate salt (I-14) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, 2-pyrrolidin-1-yl-ethylamine was used in place of $N^1$-$N^1$-dimethyl-ethane-1,2-diamine. The product was converted to the trifluoroacetate salt as described for 1-5.

4-{2-[4-Chloro-3-(3-chloro-5-cyano-phenoxy)-2-fluoro-phenyl]-acetylamino}-3-methyl-N-pyridin-3-ylmethyl-benzamide; compound with trifluoro-acetic acid (I-15) was prepared by the procedure described in steps 1 to 11 of example 3 except in step 9, 4-amino 3-methyl-benzoic acid, tert-butyl ester (39) was used in place of 4-amino 3-chloro-benzoic acid, tert-butyl ester 33b, the acylation procedure in step 1 of example 2 was utilized and in step 11, 3-aminomethyl-pyridine was used in place of $N^1$-$N^1$-dimethyl-ethane-1,2-diamine. The product was converted to the trifluoroacetate salt as described for I5.

EXAMPLE 4

4-{2[-Bromo-3-(3-cyano-5-difluoromethyl-phenoxy)-2-fluoro-phenyl]-acetylamino}-N-(2-dimethylamino-ethyl)-3-methyl-benzamide (I-18)

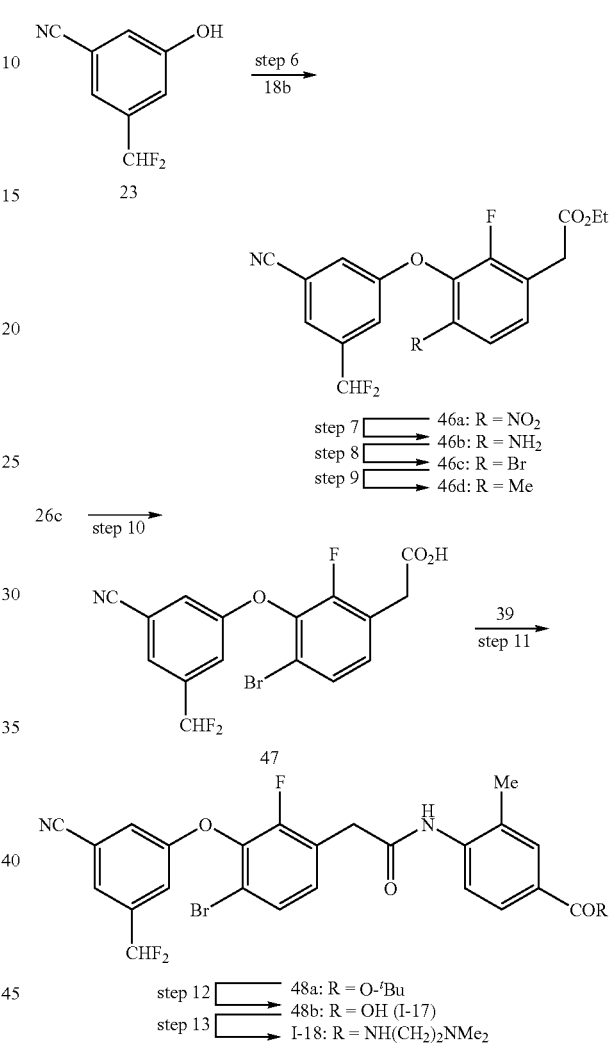

Steps 1-5 are Depicted in Scheme 3.

step 1—A solution of 20a, sodium methoxide (1 equivalent) and DMF were stirred overnight under an $N_2$ atmosphere at RT. The volatile solvents were removed in vacuo and the residue partitioned between $Et_2O$ and water. The organic phase was washed with 5% NaOH, water and brine, dried ($MgSO_4$), filtered and evaporated to afford 20b.

step 2—To a solution of 20b (60 g, 0.2256 mol) and anhydrous $Et_2O$ (1 L)cooled to −78° C. and maintained under an Ar atmosphere was added dropwise over 30 min n-BuLi (100 mL, 0.2482 mol, 2.5M in hexane). The yellow solution was stirred at −78° C. for 20 min. To the reaction mixture was added dropwise dry DMF (19 mL, 248.2 mmol) over 15 min and the reaction stirred at −78° C. for 10 min before the cooling bath was removed and the reaction allowed to warm to −30° C. over 30 min. The reaction vessel was placed in an ice-water bath and warmed to −10° C. The mixture was slowly added to an ice cold saturated aqueous $NH_4Cl$ solution (400 mL). The organic layer was separated and the aqueous phase thrice extracted with Et$_2$O. The combined extracts were washed with water, dried (MgSO$_4$), filtered and evaporated to afford an oil which solidified on standing. The crude product was purified by SiO$_2$ chromatography eluting with a hexane/EtOAc gradient (3 to 5% EtOAc) to afford 21.

step 3—A solution of 21 (10 g, 31.7 mmol), Pd[P(Ph)$_3$]$_4$(0) (2.62 g, 2.26 mmol), Zn(CN)$_2$(2.24 g, 19.0 mmol) and DMF (100 mL) under a N$_2$ atmosphere is heated to 80° C. for 5.5 h. The reaction mixture is cooled to RT and is partitioned between water and DCM. The DCM extracts are washed with water and brine and is dried (MgSO$_4$). The crude product is purified by SiO$_2$ chromatography eluting with EtOAc/hexane to afford 22a.

step 4—DAST (21.04 mL, 519 mmol) was added to a solution of 22a (15.1 g, 94 mmol) in DCM (100 mL) under nitrogen contained in a NALGENE® bottle. EtOH (0.013 mL, 0.23 mmol) was added, and the mixture was stirred for 16 h. The reaction mixture was then added slowly to an aqueous solution of saturated NaHCO$_3$. After the bubbling was finished, DCM (50 mL) was added and the layers were separated. The organic layer was washed with brine (30 mL) and dried with anhydrous MgSO$_4$. The solvent was removed and the crude product was purified by two flash chromatographies on silica gel (0% to 10% EtOAc/hexanes) to afford 22b as a white solid.

step 5—A oven dried 500 mL 3-necked flask that had been cooled under N$_2$ flow was charged with 22b (10.6 g, 57 mmol) and LiI (23.2 g, 3 equiv). NMP (160 mL) was added to the flask and the solution was heated to 175° C. flushing the reaction vessel with N$_2$ (N$_2$ inlet in one neck, bubbler on another neck). The reaction was continued for 5 d, cooled, and poured into an ammonium chloride solution. The aqueous mixture was extracted with 1:1 EtOAc/hexanes, washed with water, and dried (MgSO$_4$). The residue was purified by SiO$_2$ chromatography eluting with an EtOAc/hexane gradient (0% to 10% EtOAc) to afford 4.6 g (47%) of 23.

step 6—An oven-dried round bottom flask was charged with 23 (9.07 g, 54 mmol) and dry THF (90 mL). The solution was cooled to 0° C. under nitrogen and sodium tert-butoxide (5.27 g, 55 mmol) was added slowly over several minutes. The clear yellow solution was stirred for 10 minutes at 0° C. A separate oven-dried round bottom flask was charged with 18b (13.148 g, 54 mmol) under nitrogen and dry THF (90 mL) was added. This solution was added to the sodium phenolate solution maintained at 0° C. slowly via syringe over 10 min. After stirring at RT overnight, the reaction was slowly poured into cold, saturated aqueous KHSO$_4$ (100 mL) and extracted twice with EtOAc (2×200 mL). The organic layers were combined and washed with brine (100 mL). The solution was dried (MgSO$_4$), filtered and concentrated in vacuo. The crude product was recrystallized by dissolving in hot Et$_2$O (100 mL), adding hexane (50 mL) and storing in refrigerator for several hours. The precipitate was filtered to afford 13g of brown solid. The filtrate was concentrated and purified by SiO$_2$ column chromatography eluting with EtOAc/hexanes to afford 10g of 46a as a yellow solid. The product was combined with precipitate and the mixture recrystallized under similar conditions as described above to obtain 20g (94%) of 46a as white solid.

step 7—The bis-aryl ether 46a (16.36 g, 41.5 mmol), iron (9.732 g, 174 mmol), and NH4Cl (9.322 g, 174 mmol) were combined in a round bottom and suspended in EtOH (70 mL) and water (70 mL). The suspension was heated to reflux for 2.5 hrs, cooled to RT and filtered through CELITE®. The CELITE cake was washed repeatedly with EtOAc. The filtrate was combined and washed with brine, dried (MgSO$_4$), filtered and concentrated in vacuo. The crude material was purified by SiO$_2$ chromatography eluting with EtOAc/hexanes to afford 14.2 g (93%) of 46b as a white solid.

step 8—A 500 mL round bottom was charged the Cu(II)Br$_2$ (2.62 g, 11.7 mmol) and LiBr (3.052 g, 35.2 mmol). The mixture was purged with dry argon for 20 min. To this was added MeCN (150 mL) and stirred for 20 min at 50° C. until the solid particles were finely dispersed. To the suspension was added the tert-butyl nitrite and stirred continued for 5 min after which a solution of 46b (4.27 g, 11.72 mmol) and MeCN (40 mL) was added in a single portion. The resulting mixture was stirred at 70° C. for 1 h. The reaction mixture was cooled to 0° C. and quenched with 5% aqueous HBr (10 mL). The solution was diluted with EtOAc (200 mL) and washed with water (100 mL) and brine (50 mL). The organic layer was dried (MgSO$_4$), filtered and concentrated in vacuo. The crude material was purified by SiO$_2$ chromatography eluting with EtOAc/hexanes to obtain 2.6 g (52%) of 46c as a white solid.

Step 10 was carried out as described in step 8 of example 1 except 30b was replaced by 46c to afford the carboxylic acid 47. Steps 11-13 were carried out as described in steps 1-3 of example 2, except 47b was used in place of 34a and N$^1$-N$^1$-dimethyl-ethane-1,2-diamine was used in place of 2-pyrrolidin-1-yl-ethylamine to afford I-18.

4-{2-[4-Bromo-3-(3-cyano-5-difluoromethyl-phenoxy)-2-fluoro-phenyl]-acetylamino}-3-chloro-N-(2-pyrrolidin-1-yl-ethyl)-benzamide (I-33) was prepared as described in example 4, except 33b was used in place of 39, step 11 was carried out by the procedure in step 3 of example 1 and 2-pyrrolidin-1-yl-ethylamine was used in place of N$^1$-N$^1$-dimethyl-ethane-1,2-diamine.

4-{2-[4-Bromo-3-(3-cyano-5-difluoromethyl-phenoxy)-2-fluoro-phenyl]-acetylamino}-3-methyl-N-(2-pyrrolidin-1-yl-ethyl)-benzamide (I-34) was prepared as described for I-33 except 39 was used in place of 33b.

4-{2-[4-Bromo-3-(3-cyano-5-difluoromethyl-phenoxy)-2-fluoro-phenyl]-acetylamino}-N-((R)-2-hydroxy-propyl)-3-methyl-benzamide (I-35) was prepared as described for 1-18 except (R)-1-amino-propan-2-ol was used in place of 39.

EXAMPLE 5

4-{2-[4-Chloro-3-(3-chloro-5-cyano-phenoxy)-2-fluoro-phenyl]-acetylamino}-N-((R)-2,2-dimethyl-[1,3]dioxolan-4-ylmethyl)-3-methyl-benzamide (I-16) and 4-{2-[4-Chloro-3-(3-chloro-5-cyano-phenoxy)-2-fluoro-phenyl]-acetylamino}-N-(2,3-dihydroxy-propyl)-3-methyl-benzamide (I-20)

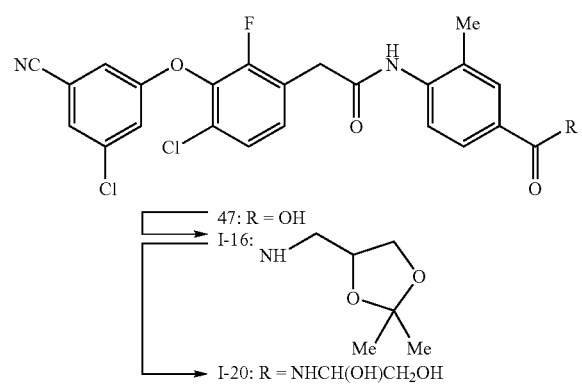

I-16 was prepared by condensation of C-(2,2-dimethyl-[1,3]dioxolan-4-yl)-methylamine (Aldrich catalog number 48,311-7) with 47 as described in step I of example 2. The acetonide I-16 (0.05 g) was suspended in a mixture of 2M HCl (0.8 mL) and dioxane (0.8 mL). The volatile materials were removed, and the white solid was purified by SiO₂ chromatography eluting with a DCM/MeOH gradient (5% to 10% MeOH) to afford 0.027 g (58%) of I-20.

EXAMPLE 6

2-[4-Bromo-3-(3-chloro-5-cyano-phenoxy)-2-fluoro-phenyl]-N-(4-methanesulfonylamino-carbonyl-2-methyl-phenyl)-acetamide (I-36)

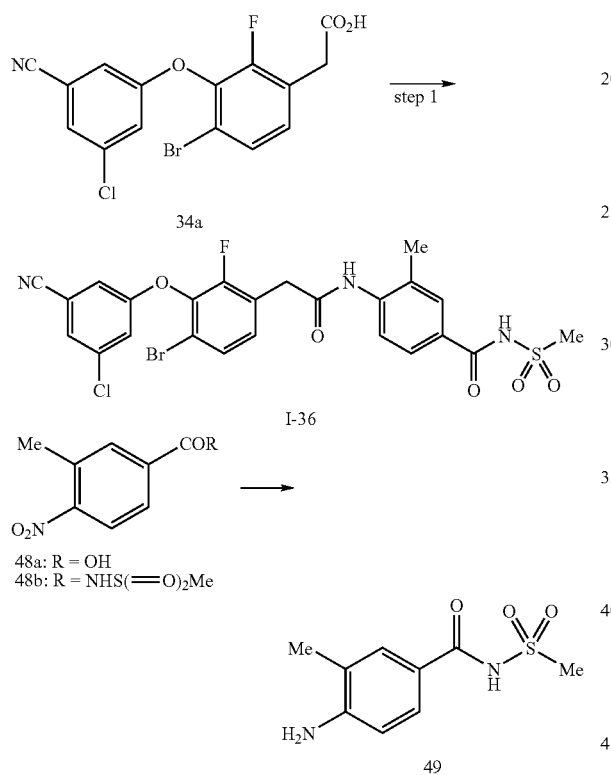

N-(4-Amino-benzoyl)-methanesulfonamide—1,1-carbonyl diimidazole (0.45 g, 1 equiv) was added to a solution of 48a (0.50 g, 2.8 mmol) in DCM (5 mL) at 0° C. After 2 h, DBU (0.41 mL, 1 equiv) and methanesulfonamide (0.26 g, 1 equiv) were added, and stirring was continued at 0 C. The solution was partitioned between DCM and brine, the organic layer was separated, and the volatile materials were evaporated. The residue was purified by SiO₂ chromatography eluting with a 1:1 mixture of hexane and EtOAc (containing 1% HOAc) to afford 0.37 g (52%) of 48b.

To a solution of 48b (0.17 g) and EtOH (7 mL) was added 10% Pd/C (17 mg) resulting suspension was agitated under H₂ (60 psi) for 16 h. The solution was filtered through CELITE®, and the volatile materials were evaporated to afford 0.12 g (85%) of 49.

step 1—To a solution 34a (0.2 g, 0.52 mmol), oxalyl chloride (0.90 mL, 2 equiv) and DCM (3 mL) was added one drop of DMF. The solution was stirred for 3 h, and the volatile materials were evaporated. The crude acid chloride was dissolved in dry acetone (3 mL) and the solution was added to a suspension of NaHCO₃ (3 equiv) and the 49 (0.12 g, 1 equiv) in acetone (3 mL). The solution was stirred for 16 h, the solvent was removed, and the residue was purified by reverse-phase HPLC to afford I-36.

EXAMPLE 7

2-[4-Bromo-3-(3-chloro-5-cyano-phenoxy)-2-fluoro-phenyl]-N-[2-chloro-4-(N'-methyl-guanidinocarbonyl)-phenyl]-acetamide (I-44)

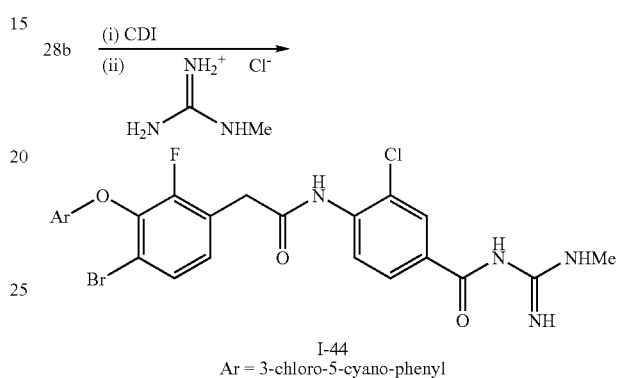

A solution of 28b (0.15 g, 0.278 mmol), CDI (1.2 eq, 0.054g) and DMF (2.5 mL) in a round-bottom flask maintained under a N₂ atmosphere was stirred for 2 h. A solution of di-iso-propylamine (2.5 eq, 0.12 mL) and methyl-guanidine HCL (2.0 eq, 0.061g) was added and the resulting solution heated at 50° C. for 3 h. The reaction was cooled to RT, poured into water and extracted with DCM (3×25mL). The combined extracts were washed with brine, dried (Na₂SO₄) and concentrated in vacuo. The resulting solid was triturated with 30%EtOAc/Hexanes to afford 0.100 g (60%) of I-44.

2-[4-bromo-3-(3-chloro-5-cyano-phenoxy)-2-fluoro-phenyl]-N-(2-chloro-4-guanidinocarbonyl-phenyl)-acetamide (I-37) was prepared analogously except guanidine HCl was used in place of N-methyl guanidine HCl. The trifluoroacetic acid salt was prepared by contacting I-38 with TFA.

2-[4-bromo-3-(3-chloro-5-cyano-phenoxy)-2-fluoro-phenyl]-N-[2-chloro-4-(N',N'-dimethyl-guanidinocarbonyl)-phenyl]-acetamide (I-46) was prepared analogously except N,N-dimethyl-guanidine HCl was used in place of N-methyl guanidine HCl.

EXAMPLE 8

N-(1-Aminomethyl-cyclopropyl)-4-{2-[4-bromo-3-(3-chloro-5-cyano-phenoxy)-2-fluoro-phenyl]-acetylamino}-3-chloro-benzamide; trifluoroacetic acid salt (I-57)

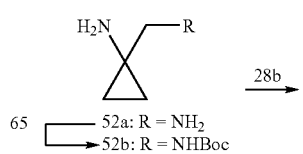

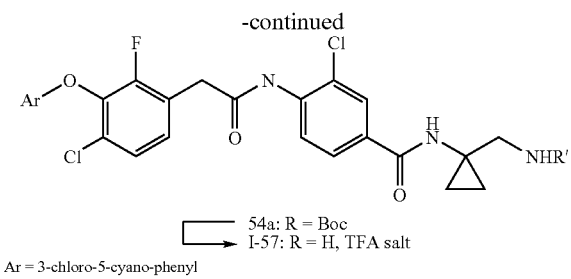

54a: R = Boc
I-57: R = H, TFA salt

Ar = 3-chloro-5-cyano-phenyl (1-Amino-cyclopropylmethyl)-carbamic acid tert-butyl ester A mixture of 1-amino-cyclopropylmethanamine dihydrochloride (F. Brackmann et al., *Eur. J Org. Chem.* 2005 3:600-609), 0.120 g, 0.75 mmol), DIPEA (0.27 mL, 1.58 mmol), phenyl tert-butylcarbonate (0.27 mL, 1.5 mmol) and EtOH (4 mL) were sealed in a tube. The tube was warmed to 85° C. for 20 h. The reaction mixture was concentrated in vacuo and the residue dissolved in DCM, poured into H$_2$O acidified with aqueous 10% HCl and the aqueous layer was thrice extracted with DCM. The aqueous layer was basified with aqueous NaOH and thrice extracted with DCM. The combined extracts were dried (Na$_2$SO$_4$), filtered and evaporated to afford 0.055 g of 52b.

A solution of 52b (0.050 g, 0.22 mmol), 28b (0.108 g, 0.2 mmol), EDCI (0.046 g, 0.24 mmol), HOBt ((0.0324 g, 0.24 mmol) and NaHCO3 (0.067 g) and DMF (3 mL) were stirred until the reaction was complete. The reaction was concentrated in vacuo, the residue dissolved in DCM and pored into H$_2$0. The aqueous phase was thrice extracted with DCM, the combined extracts dried (Na$_2$SO$_4$), filtered and evaporated. The crude product was purified by SiO$_2$ chromatography eluting with a gradient of DCM/DCM:MeOH:NH$_4$OH (60/10/1; 100 to 70% DCM) to afford 0.100 g of 54a.

A solution of 54b from the previous step, 4 N HCl in dioxane (2 mL) and dioxane (8 mL) was stirred at RT for 24 h then concentrated in vacuo. The crude product was purified by reverse phase HPLC eluting with a H$_2$O/MeCN gradient (30 to 90% MeCN containingn 0.1% aqueous TFA to afford 0.025 g of I-57.

EXAMPLE 9

Homopolymer HIV Reverse Transcriptase Assay: Inhibitor IC$_{50}$ Determination

HIV-1 RT assay was carried out in 96-well Millipore MultiScreen MADVNOB50 plates using purified recombinant enzyme and a poly(rA)/oligo(dT)$_{16}$ template-primer in a total volume of 50 μL. The assay constituents were 50 mM Tris/HCl, 50 mM NaCl, 1 mM EDTA, 6 mM MgCl$_2$, 5 μM dTTP, 0.15 μCi [$^3$H] dTTP, 5 μg/ml poly (rA) pre annealed to 2.5 μg/ml oligo (dT)$_{16}$ and a range of inhibitor concentrations in a final concentration of 10% DMSO. reactions were initiated by adding 4 nM HIV-1 RT and after incubation at 37° C. for 30 min, they were stopped by the addition of 50 μl ice cold 20%TCA and allowed to precipitate at 4° C. for 30 min. The precipitates were collected by applying vacuum to the plate and sequentially washing with 3×200 μl of 10% TCA and 2×200 μl 70% ethanol. Finally, the plates were dried and radioactivity counted in a Packard TopCounter after the addition of 25 μl scintillation fluid per well. IC$_{50}$'s were calculated by plotting % inhibition versus log$_{10}$ inhibitor concentrations.

TABLE 2

| Compound | IC$_{50}$ (μM) |
|---|---|
| I-5 | 0.0154 |
| I-10 | 0.0183 |
| I-15 | 0.0166 |
| I-20 | 0.0206 |
| I-25 | 0.0552 |
| I-30 | 0.0209 |
| I-36 | 0.0046 |

EXAMPLE 10

Heteropolymer HIV reverse Transcriptase Assay: Inhibitor IC$_{50}$ Determination RNA-dependent DNA polymerase activity was measured using a biotinylated primer oligonucleotide and tritiated dNTP substrate. Newly synthesized DNA was quantified by capturing the biotinylated primer molecules on streptavidin coated Scintillation Proximity Assay (SPA) beads (Amersham). The sequences of the polymerase assay substrate were: 18nt DNA primer, 5'-Biotin/GTC CCT GTT CGG GCG CCA-3' (SEQ. ID NO. 2); 47nt RNA template, 5'-GGG UCU CUC UGG UUA GAC CAC UCU AGC AGU GGC GCC CGA ACA GGG AC-3' (SEQ ID NO. 1). The biotinylated DNA primer was obtained from the Integrated DNA Technologies Inc. and the RNA template was synthesized by Dharmacon. The DNA polymerase assay (final volume 50 μl) contained 32 nM biotinylated DNA primer, 64 nM RNA substrate, dGTP, dCTP, dTTP (each at 5 μM), 103 nM [$^3$H]-dATP (specific activity=29 μCi/mmol), in 45 mM Tris-HCl, pH 8.0, 45 mM NaCl, 2.7 mM Mg(CH$_3$COO)$_2$, 0.045% Triton X-100 w/v, 0.9 mM EDTA. The reactions contained 5 μl of serial compound dilutions in 100% DMSO for IC50 determination and the final concentrations of DMSO were 10%. Reactions were initiated by the addition of 30 μl of the HIV-1-RT enzyme (final concentrations of 1-3 nM). Protein concentrations were adjusted to provide linear product formation for at least 30 min of incubation. After incubation at 30°C for 30 min, the reaction was quenched by addition of 50 μl of 200 mM EDTA (pH 8.0) and 2 mg/ml SA-PVT SPA beads (Amersham, RPNQ0009, reconstituted in 20 mM Tris-HCl, pH 8.0, 100 mM EDTA and 1% BSA). The beads were left to settle overnight and the SPA signals were counted in a 96-well top counter-NXT (Packard). IC$_{50}$ values were obtained by sigmoidal regression analysis using GraphPad Prism 3.0 (GraphPad Software, Inc.).

TABLE 3

| Compound | IC$_{50}$ (μM) |
|---|---|
| I-40 | 0.037 |
| I-45 | 0.0041 |
| I-50 | 0.0069 |
| I-55 | 0.0163 |

EXAMPLE 11

Pharmaceutical Compositions

Pharmaceutical compositions of the subject Compounds for administration via several routes were prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound of formula I

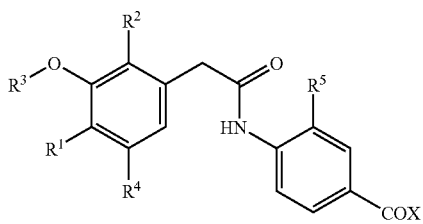

(I)

wherein:
- $R^1$ is halogen, $C_{1-6}$ alkyl, $C_{3-7}$ cycloalkyl, $C_{1-6}$ alkoxy, nitro or amino;
- $R^2$ is hydrogen or fluorine
- $R^3$ is phenyl substituted with one to three substituents independently selected from the group consisting of $C_{1-6}$ alkyl, $C_{1-6}$ haloalkyl, $C_{3-8}$ cycloalkyl, halogen, cyano or nitro;
- $R^4$ is hydrogen, $C_{1-6}$ alkyl or halogen;
- $R^5$ is hydrogen, $C_{1-6}$ alkyl, $C_{3-7}$ cycloalkyl or halogen;
- X is $NR^aR^b$;
- One of $R^a$ or $R^b$ is hydrogen, $C_{1-6}$ alkyl, $C_{3-6}$ cycloalkyl or $C_{1-6}$ hydroxyalkyl and the other of $R^a$ or $R^b$ is selected from the group consisting of
  - (a) $C_{1-6}$ alkyl,
  - (b) $C_{1-6}$ hydroxyalkyl,
  - (c) $C_{1-6}$ carboxyalkyl,
  - (d) (alkylene)$_r$NR$^c$R$^d$,
  - (e) $S(O)_2$—$C_{1-6}$ alkyl,
  - (f) $C(=NR^c)NR^fR^g$ wherein (i) $R^e$, $R^f$ and $R^g$ are independently hydrogen or $C^{1-3}$ alkyl,
  - (g) a group B

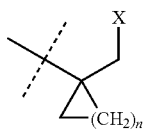

(B)

wherein n is an integer from 1 to 4 and X is as defined above, and,
  - (h) $(CH_2)_nS(O)_2(C_{1-3}$ alkyl) wherein n is an integer from 2 to 5;
- $R^c$ or $R^d$ are independently hydrogen or $C_{1-6}$ alkyl;
- r is an integer from two to six; or,
- pharmaceutically acceptable salts thereof.

2. A compound according to claim 1 wherein:
- X is $NR^aR^b$;
- $R^5$ is $C_{1-6}$ alkyl or halogen;
- either (i) $R^a$ is hydrogen and $R^b$ is selected from the group consisting of $C_{1-6}$ alkyl, $C_{1-6}$ hydroxyalkyl and (alkylene)$_r$NR$^c$R$^d$ and
- r is two to four.

3. A compound according to claim 1 wherein:
- X is $NR^aR^b$;
- $R^5$ is $C_{1-6}$ alkyl or halogen;
- $R^a$ is hydrogen and $R^b$ is $C_{1-6}$ carboxyalkyl.

4. A compound according to claim 1 wherein:
- X is $NR^aR^b$;
- $R^5$ is $C_{1-6}$ alkyl or halogen;
- $R^a$ is hydrogen or a $C_{1-6}$ hydroxyalkyl; and,
- $R^b$ is $C_{1-6}$ hydroxyalkyl.

5. A compound according to claim 1 wherein:
- X is $NR^aR^b$;
- $R^5$ is $C_{1-6}$ alkyl or halogen;
- $R^a$ is hydrogen and $R^b$ is (alkylene)$_r$NR$^c$R$^d$.

6. A compound according to claim 1 wherein:
- X is $NR^aR^b$;
- $R^5$ is $C_{1-6}$ alkyl or halogen;
- $R^a$ is hydrogen; and,
- $R^b$ is $S(O)_2$—$C_{1-6}$ alkyl.

7. A compound according to claim 1 wherein:
- $R^1$ is halogen or $C_{1-6}$ alkyl;
- $R^2$ is fluorine;
- $R^3$ is phenyl substituted with one to three substituents independently selected from the group consisting of halogen, cyano and $C_{1-3}$ haloalkyl;
- $R^4$ is hydrogen;
- $R^5$ is $C_{1-6}$ alkyl or halogen.

8. A compound according to claim 7 wherein:
- X is $NR^aR^b$;
- $R^a$ is hydrogen and $R^b$ is $C_{1-6}$ carboxyalkyl.

9. A compound according to claim 7 wherein:
X is $NR^aR^b$;
$R^a$ is hydrogen or $C_{1-6}$ hydroxyalkyl; and,
$R^b$ is $C_{1-6}$ hydroxyalkyl.

10. A compound according to claim 7 wherein:
X is $NR^aR^b$;
$R^a$ is hydrogen and $R^b$ is (alkylene)$_r$$NR^{c\,Rd}$.

11. A compound according to claim 7 wherein:
X is $NR^aR^b$;
$R^a$ is hydrogen; and,
$R^b$ is $S(O)_2$—$C_{1-6}$ alkyl.

12. A compound according to claim 7 wherein:
X is $NR^aR^b$;
$R^a$ is hydrogen and $R^b$ is $C(=NR^e)NR^fR^g$ wherein $R^e$, $R^f$ and $R^g$ are independently hydrogen or $C_{1-3}$ alkyl.

13. A pharmaceutical composition for treating an HIV-1 infection comprising a therapeutically effective quantity of a compound according to claim 1 admixed with at least one carrier, excipient or diluent.

14. A compound according to claim 1 which compound is selected from the group consisting of
- 4-{2-[4-chloro-3-(3-chloro-5-cyano-phenoxy)-2-fluoro-phenyl]-acetylamino}-N-(2-dimethylamino-ethyl)-3-methyl-benzamide;
- 4-{2-[4-chloro-3-(3-chloro-5-cyano-phenoxy)-2-fluor-phenyl]-acetylamino}-N-(2-hydroxy-ethyl)-3-methyl-benzamide;
- 4-{2-[4-chloro-3-(3-chloro-5 -cyano-phenoxy)-2-fluoro-phenyl]-acetylamino}-N —((R)-2-hydroxy-propyl)-3-methyl-benzamide;
- 4-{2-[4-bromo-3-(3-cyano-5-difluoromethyl-phenoxy)-2-fluoro-phenyl]-acetylamino}-N-(2-dimethylamino-ethyl)-3-methyl-benzamide;
- 4-{2-[4-chloro-3-(3 -chloro-5-cyano-phenoxy)-2-fluoro-phenyl]-acetylamino}-N-(2,3-dihydroxy-propyl)-3-methyl-benzamide;
- 3-chloro-4-{2-[4-chloro-3-(3-chloro-5-cyano-phenoxy)-2-fluoro-phenyl]-acetylamino}-N-(2-dimethylamino-ethyl)-benzamide;
- 2-[4-bromo-3-(3-chloro-5-cyano-phenoxy)-2-fluoro-phenyl]-N-(2-chloro-4-guanidinocarbonyl-phenyl )-acetamide;
- N-(2-amino-2-methyl-propyl)-4-{2-[4-bromo-3-(3-chloro-5-cyano-phenoxy)-2-fluoro-phenyl]-acetylamino}-3-chloro-benzamide;
- N-{2-[bis-(2-hydroxy-ethyl)-amino]-ethyl}-4-{2-[4-bromo-3-(3-chloro-5-cyano -phenoxy)-2-fluoro-phenyl]-acetylamino}-3-chloro-benzamide;
- 4-{2-[4-bromo-3-(3-chloro-5-cyano-phenoxy)-2-fluoro-phenyl]-acetylamino}-3-chloro-N-(2-dimethylamino-1-methyl-ethyl)-benzamide;
- 2-[4-bromo-3-(3-chloro-5-cyano-phenoxy)-2-fluoro-phenyl]-N-[2-chloro-4-(N'-methyl-guanidinocarbonyl)-phenyl]-acetamide;
- 2-[4-bromo-3-(3-chloro-5-cyano-phenoxy)-2-fluoro-phenyl]-N-[2-chloro-4-(N',N'-dimethyl-guanidinocarbonyl)-phenyl]-acetamide;
- N-(2-amino-1,1-dimethyl-ethyl)-4-{2-[4-bromo-3-(3-chloro-5-cyano-phenoxy)-2-flouro-phenyl]-acetylamino}-3-chloro-benzamide;
- 4-{2-[4-bromo-3-(3-chloro-5-cyano-phenoxy)-2-fluoro-phenyl]-acetylamino}-3-chloro-N-(1-hydroxymethyl-cyclopropyl)-benzamide;
- 4-{2-[4-bromo-3-(3-chloro-5-cyano-phenoxy)-2-fluoro-phenyl]-acetylamino}-3-chloro-N-(2-methanesulfonyl-ethyl)-benzamide;
- N-(1-aminomethyl-cyclopropyl)-4-{2-[4-bromo-3-(3-chloro-5-cyano-phenoxy)-2-fluoro-phenyl]-acetylamino}-3-chloro-benzamide; and,
- 4-{2-[4-bromo-3-(3-chloro-5-cyano-phenoxy)-2-fluoro-phenyl]-acetylamino}-3-chloro-N-(2-hydroxy-1-hydroxymethyl-1-methyl-ethyl)-benzamide; or a pharmaceutically acceptable salt thereof.

\* \* \* \* \*

SEQUENCE LISTING

```
<160> NUMBER OF SEQ ID NOS: 2

<210> SEQ ID NO 1
<211> LENGTH: 47
<212> TYPE: RNA
<213> ORGANISM: Artificial
<220> FEATURE:
<223> OTHER INFORMATION: RNA template for HIV reverse transcriptase
      assay
```

```
-continued

<400> SEQUENCE: 1
gggucucucu gguuagacca cucuagcagu ggcgcccgaa cagggac          47

<210> SEQ ID NO 2
<211> LENGTH: 18
<212> TYPE: DNA
<213> ORGANISM: artificial
<220> FEATURE:
<223> OTHER INFORMATION: 5'-biotinylated DNA primer for HIV reverse
      transcriptase assay
<220> FEATURE:
<221> NAME/KEY: misc_feature
<222> LOCATION: (1)..(1)
<223> OTHER INFORMATION: 5' g is biotinylated guanosine

<400> SEQUENCE: 2
gtccctgttc gggcgcca                                        18
```